(12) United States Patent
Guo et al.

(10) Patent No.: US 10,675,015 B2
(45) Date of Patent: Jun. 9, 2020

(54) SYSTEMS, DEVICES AND METHODS FOR DELIVERING TRANSFASCIAL SUTURE IMPLANTS FOR SECURING SURGICAL MESH TO TISSUE

(71) Applicant: Ethicon, Inc., Somerville, NJ (US)

(72) Inventors: Jianxin Guo, Livingston, NJ (US); Simon Cohn, Lebanon, NJ (US); Michael Cardinale, Morristown, NJ (US)

(73) Assignee: Ethicon, Inc., Somerville, NJ (US)

( * ) Notice: Subject to any disclaimer, the term of this patent is extended or adjusted under 35 U.S.C. 154(b) by 327 days.

(21) Appl. No.: 15/647,397

(22) Filed: Jul. 12, 2017

(65) Prior Publication Data
US 2019/0015091 A1 Jan. 17, 2019

(51) Int. Cl.
*A61B 17/04* (2006.01)
*A61B 17/00* (2006.01)
*A61F 2/00* (2006.01)

(52) U.S. Cl.
CPC ...... *A61B 17/0401* (2013.01); *A61B 17/0469* (2013.01); *A61B 17/0483* (2013.01);
(Continued)

(58) Field of Classification Search
CPC ............ A61B 17/0401; A61B 17/0469; A61B 2017/00336; A61B 2017/0417;
(Continued)

(56) References Cited

U.S. PATENT DOCUMENTS 5,269,809 A * 12/1993 Hayhurst ........... A61B 17/0401
606/232
5,626,614 A 5/1997 Hart
(Continued)

FOREIGN PATENT DOCUMENTS

EP 1568327 8/2005
WO 2014190080 11/2014
(Continued)

OTHER PUBLICATIONS

Kumar T-Anchors, http://www.nashvillesurg.com/kumar-t-anchors--.html, Nashville Surgical Instruments, Springfield, TN, 2017, 5 pages.
(Continued)

*Primary Examiner* — Phong Son H Dang

(57) ABSTRACT

A system for deploying a suture implant includes a delivery device and a suture implant coupled with the distal end of the delivery device. The suture implant includes a suture and a slip knot that defines a suture loop, the slip knot defining a dynamic end of the suture loop that is located opposite a closed end of the suture loop. The suture implant includes a tissue anchor having first and second openings, whereby the closed end of the suture loop passes through the first and second openings for securing the tissue anchor to the suture loop. A tensioner is secured to the first end of the suture, and a pledget, located between the tensioner and the tissue anchor, is secured to the second end of the suture. Pulling the tensioner away from the tissue anchor slides the pledget and the slip knot toward the tissue anchor for shortening the length of the suture loop and reducing the distance between the pledget and the tissue anchor.

23 Claims, 28 Drawing Sheets

(52) U.S. Cl.
CPC ............ *A61B 2017/00336* (2013.01); *A61B 2017/044* (2013.01); *A61B 2017/0406* (2013.01); *A61B 2017/0409* (2013.01); *A61B 2017/0414* (2013.01); *A61B 2017/0416* (2013.01); *A61B 2017/0417* (2013.01); *A61B 2017/0419* (2013.01); *A61B 2017/0438* (2013.01); *A61B 2017/0441* (2013.01); *A61B 2017/0445* (2013.01); *A61B 2017/0458* (2013.01); *A61B 2017/0464* (2013.01); *A61B 2017/0475* (2013.01); *A61B 2017/0496* (2013.01); *A61F 2/0063* (2013.01); *A61F 2220/0016* (2013.01)

(58) Field of Classification Search
CPC .... A61B 2017/0458; A61B 2017/0496; A61B 2017/0464; A61B 2017/0419; A61B 2017/0409; A61B 2017/044; A61B 17/0483; A61B 2017/0441; A61B 2017/0475; A61B 2017/0445; A61B 2017/0438; A61B 2017/0414; A61B 2017/0406; A61B 2017/0416; A61F 2220/0016; A61F 2/0063
See application file for complete search history.

(56) References Cited

U.S. PATENT DOCUMENTS

| | | | |
|---|---|---|---|
| 6,544,267 B1 | 4/2003 | Cole et al. | |
| 6,635,073 B2* | 10/2003 | Bonutti | A61B 17/0401 606/216 |
| 7,390,332 B2* | 6/2008 | Selvitelli | A61B 17/0401 606/144 |
| 7,455,683 B2 | 11/2008 | Geissler et al. | |
| 7,651,509 B2* | 1/2010 | Bojarski | A61B 17/06109 606/139 |
| 7,887,551 B2* | 2/2011 | Bojarski | A61B 17/0401 606/139 |
| 7,909,851 B2* | 3/2011 | Stone | A61B 17/0401 606/232 |
| 8,128,698 B2* | 3/2012 | Bentley | A61B 17/064 623/17.11 |
| 8,292,921 B2* | 10/2012 | Stone | A61B 17/0401 606/232 |
| 8,298,247 B2* | 10/2012 | Sterrett | A61B 17/0469 606/103 |
| 8,366,744 B2* | 2/2013 | Bojarski | A61B 17/0401 606/232 |
| 8,512,375 B2* | 8/2013 | Torrie | A61B 17/0401 606/232 |
| 8,623,051 B2* | 1/2014 | Bojarski | A61B 17/0401 24/129 R |
| 8,696,704 B2 | 4/2014 | Selvitelli et al. | |
| 8,702,753 B2 | 4/2014 | Mikkaichi et al. | |
| 8,790,356 B2 | 7/2014 | Darois et al. | |
| 8,790,369 B2* | 7/2014 | Orphanos | A61B 17/0401 606/232 |
| 8,828,052 B2* | 9/2014 | Caborn | A61B 17/0401 606/232 |
| 8,828,054 B2* | 9/2014 | Caborn | A61B 17/0401 606/232 |
| 8,961,538 B2* | 2/2015 | Koogle, Jr. | A61B 17/0401 606/139 |
| 9,095,331 B2 | 8/2015 | Hernandez et al. | |
| 9,149,266 B2 | 10/2015 | Lamson et al. | |
| 9,173,651 B2* | 11/2015 | Stone | A61B 17/0401 |
| 9,220,493 B2* | 12/2015 | Hart | A61B 17/0401 |
| 9,220,494 B2* | 12/2015 | Bojarski | A61B 17/0469 |
| 9,295,461 B2* | 3/2016 | Bojarski | A61B 17/06109 |
| 9,386,982 B2* | 7/2016 | Caborn | A61B 17/0483 |
| 9,517,060 B2* | 12/2016 | Flint | A61B 17/0466 |
| 9,545,251 B2* | 1/2017 | Bojarski | A61B 17/0467 |
| 9,757,113 B2* | 9/2017 | Pasquali | A61B 17/0401 |
| 9,833,231 B2* | 12/2017 | Bojarski | A61B 17/0469 |
| 10,058,320 B2* | 8/2018 | Oren | A61B 17/0401 |
| 10,251,637 B2* | 4/2019 | Stone | A61B 17/0401 |
| 10,363,024 B2* | 7/2019 | Koogle, Jr. | A61B 17/0401 |
| 2005/0033363 A1* | 2/2005 | Bojarski | A61F 2/0811 606/228 |
| 2005/0251205 A1* | 11/2005 | Ewers | A61B 17/10 606/232 |
| 2005/0261709 A1 | 11/2005 | Sakamoto et al. | |
| 2005/0283246 A1 | 12/2005 | Cauthen et al. | |
| 2006/0190042 A1* | 8/2006 | Stone | A61B 17/0401 606/232 |
| 2006/0293709 A1* | 12/2006 | Bojarski | A61B 17/0401 606/232 |
| 2007/0027476 A1* | 2/2007 | Harris | A61B 17/0401 606/232 |
| 2007/0083236 A1* | 4/2007 | Sikora | A61B 17/0401 606/232 |
| 2009/0088797 A1* | 4/2009 | Crombie | A61B 17/0401 606/232 |
| 2009/0112232 A1 | 4/2009 | Carinich et al. | |
| 2009/0259260 A1* | 10/2009 | Bentley | A61B 17/0487 606/300 |
| 2011/0082471 A1 | 4/2011 | Holcomb et al. | |
| 2011/0306989 A1 | 12/2011 | Darois et al. | |
| 2012/0116452 A1* | 5/2012 | Stone | A61B 17/0401 606/232 |
| 2012/0323275 A1 | 12/2012 | Crombie et al. | |
| 2014/0088644 A1 | 3/2014 | Flint | |
| 2014/0296881 A1 | 10/2014 | Ranucci et al. | |
| 2014/0350599 A1* | 11/2014 | Torrie | A61B 17/0401 606/232 |
| 2018/0085109 A1* | 3/2018 | Petry | A61B 17/0401 |

FOREIGN PATENT DOCUMENTS

| | | |
|---|---|---|
| WO | 2015128835 | 9/2015 |
| WO | 2015156826 | 10/2015 |

OTHER PUBLICATIONS

International Search Report issued in corresponding International Application No. PCT/US2018/041353, dated Oct. 17, 2018, 6 pages.

* cited by examiner

SYSTEMS, DEVICES AND METHODS FOR DELIVERING TRANSFASCIAL SUTURE IMPLANTS FOR SECURING SURGICAL MESH TO TISSUE

BACKGROUND OF THE INVENTION

Field of the Invention

The present patent application is generally directed to systems, devices and methods for attaching prosthetic devices to tissue, and is more particularly directed to systems, devices and methods for attaching surgical mesh to the surface of tissue during hernia repair procedures.

Description of the Related Art

The anterior abdominal wall is comprised of a muscle layer, surrounded by strong connective tissue known as fascia. Adipose tissue (fat) and dermal layers (skin) are located on the outside of the muscle layer. A weakness in the abdominal wall, for example caused by a former surgical incision, may allow the internal organs to pass through, causing a hernia. Hernias are relatively common and may cause pain or strangulation of the bowel, in which blood flow to the tissue is restricted. Such hernias often need to be repaired.

Many methods of hernia repair are known. Among the most popular is the use of a mesh barrier placed on the inside of the abdominal wall to cover the defect. This procedure can be accomplished through open surgery, however minimally invasive surgery is becoming increasingly popular as an approach to treat this condition.

The minimally invasive laparascopic surgical techniques typically require only a few small incisions (0.5-1.5 centimeters) in the abdomen, instead of a larger incision typical of open surgery. A trocar (i.e., a tube-shaped port which typically has a 5-12 millimeter internal diameter) is inserted into each incision. The abdomen is then inflated with insufflation gas (e.g., carbon dioxide), and a small camera and surgical tools are advanced through the trocars. The image from the camera is typically projected on a monitor in the operating room, allowing the surgeon to see the inside of the cavity and the extent of the defect in the abdominal wall. Laparoscopic tools are generally designed with a long wand-like distal end that is inserted into the cavity through the trocar. The wand-like distal end is then positioned manually by the surgeon and may be activated, for example, by the squeeze of a trigger or other suitable means.

For cases of laparoscopic ventral hernia repair, the surgeon first identifies the hernia defect before cutting the mesh to be about 3-5 centimeters longer in diameter than the size of the hole itself. The mesh is then inserted into the abdominal cavity through a trocar, and secured to the anterior abdominal wall in such a fashion that it covers the hernia defect. To provide for a secure fixation of the mesh to the anterior abdominal wall, sutures are often used to secure the mesh to the abdominal wall. The sutures are placed on the mesh and then advanced through the abdominal wall until they are visible outside the abdominal wall. The sutures are then tied off against the abdominal wall. Generally, 4 or more sutures are used to fix the mesh to the abdominal wall, depending on the size of defect. Tacks are then typically applied near the perimeter of the mesh to fix the mesh to the abdominal wall. The tacks are placed at close intervals, preventing the bowels (or other organs) from passing between the mesh and the abdominal wall. Such tacks come in several varieties and may be made of metal or absorbable materials. Typical examples can be found, for example, in U.S. Pat. Nos. 6,036,701, 5,904,696, and 6,837,893, the disclosures of which are hereby incorporated by reference herein.

The laparoscopic method for repairing hernias may cause several problems. For example, transfascial sutures can often cause excessive post-operative pain. Specifically, internal forces exerted on the mesh are typically transferred to the muscle layer through these sutures. The sutures, in turn, concentrate these forces causing pain. Moreover, sutures have relatively low compliance compared to abdominal tissues, and therefore sutures may "pinch" when the muscle tissue contracts, similarly causing irritation to surrounding tissue. Furthermore, metal tacks (as described above) may occasionally dislodge from the abdominal wall, permitting them to irritate other tissue as they move within the body. Without the fasteners to hold the mesh in place, the mesh may come loose. These events may lead to additional complications, and possibly additional surgery.

During conventional laparoscopic ventral hernia repair procedures, transfascial sutures are often used to both position and secure a surgical mesh in place. First, before the surgical mesh is inserted into an abdominal cavity, several sutures are attached and/or tied manually to the surgical mesh at predetermined locations. The surgical mesh is then rolled into a tight cylindrical shape, secured using an endoscopic gripping tool, and passed through a trocar for insertion into the abdominal cavity. After the surgical mesh has been inserted into the abdominal cavity, it is unrolled, and a suture passer is inserted through corresponding skin cuts on the abdominal wall to pass the suture limbs out. For each transfascial suture location, the suture passer has to be inserted twice at different angles to pass the two suture limbs out of the body in order to form a suture loop. The two suture limbs are tied to form suture knots, and the suture knots are buried under the skin.

There are a number of problems associated with the surgical technique described above. First, sutures have to be pre-attached or tied to the surgical mesh before the surgical mesh is inserted into the peritoneal cavity, which is time consuming. Second, skin cuts are required for the suture passer to form openings for the suture limbs, which is a possible source of infection. Third, each suture location requires two suture limbs to be passed outside the body for forming a suture loop, which is time consuming. Fourth, for each suture location, suture knots must be formed, which is time consuming. Fifth, when the suture knots are formed, the suture loop may entrap tissue and/or nerves, which may cause acute or chronic pain to the patient.

Thus, in spite of the above advances, there remains a continuing need for improved systems, devices and methods that eliminate the requirement to pass sutures from inside the body to outside the body, and that eliminate the requirement to make suture knots. There also remains a need for improved systems, devices and methods that simplify the steps required for surgeons to apply transfascial sutures, while still providing for secure fixation to the surgical mesh. In addition, there remains a need for improved systems, devices and methods using transfascial sutures that eliminate the need to make skin cuts, which may result in secondary infections. There also remains a need for improved systems, devices and methods of using transfascial sutures that eliminate the presence of suture loops that may entrap tissue and nerves in order to reduce the potential for acute and chronic pain to the patient. There also remains a need for systems, devices and methods that reduce the length of hernia repair procedures.

For open hernia repair procedure, there remains a need for improved systems, devices and methods that provide for easy access to surgical sites, that increase visibility for the surgeon to the surgical site, and that eliminate the need for excess dissection of the surgical pocket in order for the surgeon to pass sutures. There also remains a need for improved systems, devices and methods that significantly reduce the length of open repair surgical procedures by providing for easy application of suture, with no requirement to tie knots.

SUMMARY OF THE INVENTION

In one embodiment, a system for deploying a suture implant includes a delivery device having an elongated shaft with a distal end, and a suture implant coupled with the distal end of the elongated shaft.

In one embodiment, the suture implant may include a suture having a first end, a second end, and a slip knot located between the first and second ends that defines a suture loop having a length, whereby the slip knot defines a dynamic end of the suture loop that is located opposite a closed end of the suture loop.

In one embodiment, the suture implant preferably includes a tissue anchor having first and second openings that are spaced from one another, whereby the closed end of the suture loop passes through the first and second spaced openings for securing the tissue anchor to the suture loop, a tensioner secured to the first end of the suture, and a pledget secured to the second end of the suture and located between the tensioner and the tissue anchor. In one embodiment, the slip knot is located between the pledget and the tissue anchor.

In one embodiment, pulling the tensioner away from the tissue anchor slides the pledget and the slip knot toward the tissue anchor for shortening the length of the suture loop and reducing the distance between the pledget and the tissue anchor.

In one embodiment, the tissue anchor has a proximal end with an angled face and a distal end with a tissue piercing point.

In one embodiment, the tissue anchor has a mid-section located between the proximal and distal ends thereof that defines a closed outer surface at a top side of the tissue anchor that is bounded by the first and second openings.

In one embodiment, the tissue anchor includes an elongated conduit that extends from the proximal end to the distal end of the tissue anchor. In one embodiment, the first opening includes a proximal elongated slot that is open at the top side of the tissue anchor and that extends from the angled face to the mid-section of the tissue anchor. In one embodiment, the second opening includes a distal elongated slot that is open at the top side of the tissue anchor and that extends from the tissue piercing point to the mid-section of the tissue anchor.

In one embodiment, the closed end of the suture loop passes through the proximal and distal elongated slots and under the mid-section of the tissue anchor for coupling the tissue anchor with the suture loop. In one embodiment, the tissue anchor is free to rotate and/or toggle into different orientations relative to the closed end of the suture loop.

In one embodiment, the pledget has a first end with an angled face and a second end having a recess. In one embodiment, the pledget includes an elongated slot that extends from the angled face of the pledget toward the second end of the pledget, and an elongated conduit that extends from the elongated slot to the recess at the second end of the pledget. In one embodiment, the second end of the suture passes in series through the elongated slot, the elongated conduit and into the recess. In one embodiment, the second end of the suture includes a knot disposed in the recess of the pledget. In one embodiment, the knot has a larger diameter than the diameter of the elongated conduit of the pledget.

In one embodiment, after the tensioner is pulled away from the tissue anchor to apply tension to the suture, the elongated slot of the pledget preferably opposes the top side of the tissue anchor and the slip knot is desirably aligned with the elongated slot.

In one embodiment, the tensioner has a proximal end, a distal end, a recess located at the proximal end, and a suture channel extending from a distal end of the recess to the distal end of the tensioner. In one embodiment, the recess of the tensioner has a larger diameter than the suture channel of the tensioner. In one embodiment, the first end of the suture passes in series through the suture channel and into the recess of the tensioner. In one embodiment, the first end of the suture has a knot disposed in the recess of the tensioner, the knot having a larger diameter than the diameter of the suture channel of the tensioner.

In one embodiment, a delivery device for the suture implant disclosed herein preferably includes a cartridge for the suture implant, which may be secured to the distal end of the elongated shaft of the delivery device. In one embodiment, the cartridge has a tube shaped body with a proximal end and a distal end, a tensioner channel at the proximal end of the tube shaped body adapted to receive the tensioner of the suture implant, a proximal suture slot that extends from the proximal end toward the distal end of the tube shaped body, a pledget opening located at a distal end of the proximal suture slot for inserting the pledget into the tube shaped body, and a distal suture slot that extends from the pledget opening to the distal end of the tube shaped body. In one embodiment, the pledget opening is wider than the width of the proximal and distal suture slots.

In one embodiment, the cartridge has a distal end cap secured to the distal end of the tube shaped body. The distal end cap preferably has a larger outer diameter than an outer diameter of the tube shaped body to define a stop at a proximal end of the distal end cap.

In one embodiment, the cartridge includes a pair of pins projecting away from one another on opposite sides of the tube shaped body. In one embodiment, the distal end of the elongated shaft of the delivery device desirably includes a pair of slots adapted to receive the pins for securing the cartridge to the distal end of the elongated shaft of the delivery device.

In one embodiment, a cartridge for a suture implant may include an upper channel that extends along the length of the tube shaped body to the distal end of the distal end cap, and a lower channel that extends along the length of the tube shaped body to the distal end of the distal end cap. In one embodiment, the pledget is disposed in the upper channel, the tissue anchor is disposed in the lower channel, the suture loop extends between the pledget and the tissue anchor, and the tensioner is disposed in the tensioner channel.

In one embodiment, the slip knot is disposed within the upper channel and is located between the pledget and the tissue anchor.

In one embodiment, the tensioner channel is in axial alignment with the upper channel, and the first end of the suture material extends in the tensioner channel between the pledget and the tensioner.

In one embodiment, the cartridge has a hard stop disposed between a distal end of the tensioner channel and a proximal end of the upper channel. In one embodiment, the tensioner is proximal to the hard stop and the pledget is distal to the hard stop.

In one embodiment, a delivery device for a suture implant may include a tissue anchor driver disposed within the lower channel of the cartridge, and an actuator for advancing the tissue anchor driver toward the distal end of the elongated shaft for dispensing the tissue anchor from the lower channel of the cartridge.

In one embodiment, a system for deploying a suture implant into tissue desirably includes a delivery device having a handle, an elongated shaft extending from the handle, a driver disposed within the elongated shaft, and an actuator coupled with the driver for advancing the driver toward the distal end of the elongated shaft. In one embodiment, a suture implant is preferably disposed at the distal end of the elongated shaft.

In one embodiment, the suture implant desirably includes a suture having a first end, a second end, and a slip knot located between the first and second ends to define a suture loop having a length. In one embodiment, the slip knot defines a dynamic end of the suture loop that is opposite a closed end of the suture loop.

In one embodiment, the suture implant includes a tissue anchor having first and second openings that are spaced from one another, whereby the closed end of the suture loop passes through the first and second spaced openings for securing the tissue anchor to the suture loop.

In one embodiment, the suture implant has a tensioner secured to the first end of the suture, and a pledget secured to the second end of the suture and located between the tensioner and the tissue anchor.

In one embodiment, the slip knot is located between the pledget and the tissue anchor. In one embodiment, the tensioner is configured to be pulled away from the tissue anchor for sliding the pledget and the slip knot toward the tissue anchor for shortening the length of the suture loop and reducing the distance between the pledget and the tissue anchor.

In one embodiment, a distal end of the driver is aligned with the tissue anchor, and an actuator (e.g., a trigger) is engageable for dispensing the tissue anchor from the distal end of the elongated shaft.

In one embodiment, a cartridge for a suture implant is secured to the distal end of an elongated shaft of a delivery device. In one embodiment, the suture implant preferably includes a tube shaped body having a proximal end, a distal end, and a length that extends between the proximal and distal ends thereof, a tensioner channel at the proximal end of the tube shaped body, a proximal suture slot that extends from the proximal end of the tube shaped body toward the distal end of the tube shaped body, a pledget opening located at a distal end of the proximal suture slot for inserting the pledget into the tube shaped body, and a distal suture slot that extends from the pledget opening to the distal end of the tube shaped body, whereby the pledget opening is wider than the width of the proximal and distal suture slots.

In one embodiment, the tube shaped body of the cartridge preferably includes an upper channel that extends along the length of the tube shaped body to the distal end of the tube shaped body, whereby the upper channel is in axial alignment with the tensioner channel.

In one embodiment, the tube shaped body has a hard stop that is disposed between a distal end of the tensioner channel and a proximal end of the upper channel.

In one embodiment, the tube shaped body has a lower channel that extends along the length of the tube shaped body to the distal end of the tube shaped body.

In one embodiment, the pledget is disposed in the upper channel, and the tensioner is disposed in the tensioner channel. In one embodiment, the tensioner is proximal to the hard stop and the pledget is distal to the hard stop.

In one embodiment, the tissue anchor is disposed in the lower channel, the suture loop extends between the tissue anchor in the lower channel and the pledget in the upper channel, the slip knot is disposed within the upper channel, and the first end of the suture material extends in the tensioner channel between the pledget and the tensioner.

In one embodiment, a system for deploying a suture implant into tissue desirably includes a delivery device having an elongated shaft, a driver disposed within the elongated shaft, and an actuator for advancing the driver toward the distal end of the elongated shaft.

In one embodiment, the system includes a suture implant cartridge secured to the distal end of the elongated shaft, and a suture implant loaded into the suture implant cartridge.

In one embodiment, the suture implant preferably includes a suture having a first end, a second end, and a slip knot located between the first and second ends to define a suture loop having a length, whereby the slip knot defines a dynamic end of the suture loop that is opposite a closed end of the suture loop.

In one embodiment, the suture implant includes a tissue anchor having first and second openings that are spaced from one another, whereby the closed end of the suture loop passes through the first and second spaced openings for securing the tissue anchor to the suture loop, a tensioner secured to the first end of the suture, a pledget secured to the second end of the suture and being located between the tensioner and the tissue anchor, and the slip knot being located between the pledget and the tissue anchor.

In one embodiment, the delivery device preferably has a first dispensing stage during which the driver moves distally for dispensing the tissue anchor from the cartridge, and a second dispensing stage during which the tensioner is pulled away from the tissue anchor for sliding the pledget and the slip knot toward the tissue anchor to shorten the length of the suture loop and reduce the distance between the pledget and the tissue anchor.

In one embodiment, the delivery devices, cartridges, and transfascial suture implants disclosed herein will preferably eliminate the need for passing sutures from inside the body to outside the body, and will eliminate the need for suture knot tying, which will significantly reduce operating room time and the length of surgical procedures. The delivery devices, cartridges, and transfascial suture implants disclosed herein will also provide easier ways for surgeons to apply transfascial sutures, while still providing for secure fixation of surgical meshes to tissue.

In one embodiment, the delivery devices, cartridges, and transfascial suture implants disclosed herein desirably eliminating the need to make skin cuts, which may cause secondary infections, and eliminates suture loops that entrap tissue and nerves, thereby reducing acute and chronic pain to the patient.

In one embodiment, for open repair procedures, the delivery devices, cartridges, and transfascial suture implants disclosed herein provide easy access to surgical sites, increases visibility for the surgeon at the surgical site, and eliminates the need for excess dissection of a surgical pocket in order for the surgeon to pass sutures. The delivery devices, cartridges, and transfascial suture implants disclosed herein also significantly reduce the length of time required for open repair procedures due to easy application of the suture implants and the lack of a requirement to tie knots for each suture.

In one embodiment, a transfascial suturing device preferably includes a tissue anchor having a penetration entry point with a passage channel for a suture loop, a mesh pledget to hold and/or fixate a surgical mesh, a suture loop connecting the tissue anchor and the pledget, the suture loop having a slip knot, and a tensioner extending from the suture loop.

In one embodiment, the tissue anchor has one or more penetration points so that the tissue anchor may easily penetrate surgical mesh and/or tissues under the skin layer.

In one embodiment, the suture passage in the tissue anchor is designed for easy toggling of the tissue anchor when the suture is pulled and tightened.

In one embodiment, the slip knot is self-locking or locked by tensioning the suture loop.

In one embodiment, the tensioner is designed for easy tensioning of the suture and cinching the pledget for secure fixation.

In one embodiment, the pledget is designed to hide and/or cover the slip knot to prevent possible irritation and adhesion by the exposed knot.

In one embodiment, the suture implant is designed for an insert and pull application, with no manual knotting required.

In one embodiment, both sides of the suture loop travel through a single path, which will not entrap tissue and nerves, thereby reducing and/or eliminating pain for the patient.

The slip knot may be a Weston type slip knot, or a Roeder type slip knot.

In one embodiment, the suture, the anchor and/or the pledget may be absorbable or non-absorbable In one embodiment, a delivery device for a use during an open hernia repair procedure may include a handle, a curved or straight cannula or driver extending from the handle, whereby the cannula or driver has a distal end configured to releasably secure a tissue anchor to the distal end.

In one embodiment, the tensioner is retained on a proximal end of the delivery device (e.g., the handle or shaft).

In one embodiment, the delivery device may have a release button for releasing the tissue anchor from the distal end of the shaft/cannula.

In one embodiment, the tissue anchor may be self-stripping or may be pushed off the end of the shaft using a pushing rod coupled with a releasing button.

In one embodiment, a delivery device has a curved body (e.g., a curved or angulated shaft) that provides for easy access to a surgical site, less dissection for suturing, and good visibility.

In one embodiment, a delivery device provides for automatic tensioning of the suture and cinching the pledget when retracting the delivery device.

In one embodiment, no manual knots are required, which significantly saves OR time.

In one embodiment, the tissue anchor locks up on the fascial layer to provide for secure fixation.

In one embodiment, a transfascial suture delivery device for use during laparoscopic procedures may include a handle, a retractable cannula, a reloadable cartridge containing a transfascial suture implant, and a tissue anchor driver.

In one embodiment, the delivery device stores energy to drive the tissue anchor to penetrate the surgical mesh. In one embodiment, the tissue anchor driver is triggered by the retractable cannula. In one embodiment, a delivery device may have an attached cutting blade (e.g., attached to the cartridge) for cutting the suture after tensioning and/or cinching.

In one embodiment, the cannula has an outer diameter of about 5 mm.

In one embodiment, energy is stored by pulling a retraction button. The release of the stored energy may be triggered by retracting the cannula/shaft. The stored energy is preferably used to assist the tissue anchor in penetrating the surgical mesh layer.

In one embodiment, once the tissue anchor penetrates the surgical mesh, a user may continue to push the handle so that the tissue anchor may penetrate the other tissue layers until the tissue anchor reaches the skin. This desirably allows the user to control penetration depth.

In one embodiment, a user may retract the delivery device to position the tissue anchor at a desired tissue layer (e.g., the anterior fascia layer).

In one embodiment, the tissue anchor desirably toggles when tensioning the suture, whereupon the tissue anchor locks up on the fascia layer.

In one embodiment, a delivery device has a no trigger design. In one embodiment, only a push and pull action is required for deploying the suture implant. In one embodiment, the delivery device is retracted (i.e., pulled back toward the user) to tension and/or cinch the pledget for fixation.

In one embodiment, an implant device is loaded into a cartridge, which, in turn, is secured to a distal end of an elongated shaft of a delivery device. In one embodiment, the cartridge is reloadable with another suture implant so that that cartridge is re-useable.

In one embodiment, a delivery device preferably includes a reloadable cartridge containing a transfascial suture implant with a self-stripping tissue anchor.

In one embodiment, a feature on the proximal end of a reloadable cartridge allows the cartridge to be positioned and maneuvered by Laparoscopic graspers.

In one embodiment, use of small cartridges in conjunction with a standard grasper may reduce device size and cost.

In one embodiment, the tissue anchor may have threads to provide for a screw type tissue anchor. In one embodiment, providing threads on a screw type tissue anchor may increase holding force.

In one embodiment, a suture implant may include a suture wrapped around a central shaft of a delivery device and a pledget may be held in a pocket.

In one embodiment, a delivery device may have a collapsible outer sheath. The collapsible outer sheath may help to retain a self-stripping tissue anchor, manage a suture, and/or help a user to gauge the insertion depth of a tissue anchor.

In one embodiment, a cartridge that contains a suture implant may have an interrupted cartridge body. In one embodiment, the interruptions in the cartridge body may help with assembly of the suture implant onto the cartridge.

In one embodiment, a reloadable cartridge containing a transfascial suture implant has a self-stripping tissue anchor.

In one embodiment, a delivery device has an articulating shaft, which may help a user to deliver a tissue anchor along an axis that is perpendicular to the tissue.

These and other preferred embodiments of the present invention will be described in more detail below.

DETAILED DESCRIPTION OF PREFERRED EMBODIMENTS

Figure 1:
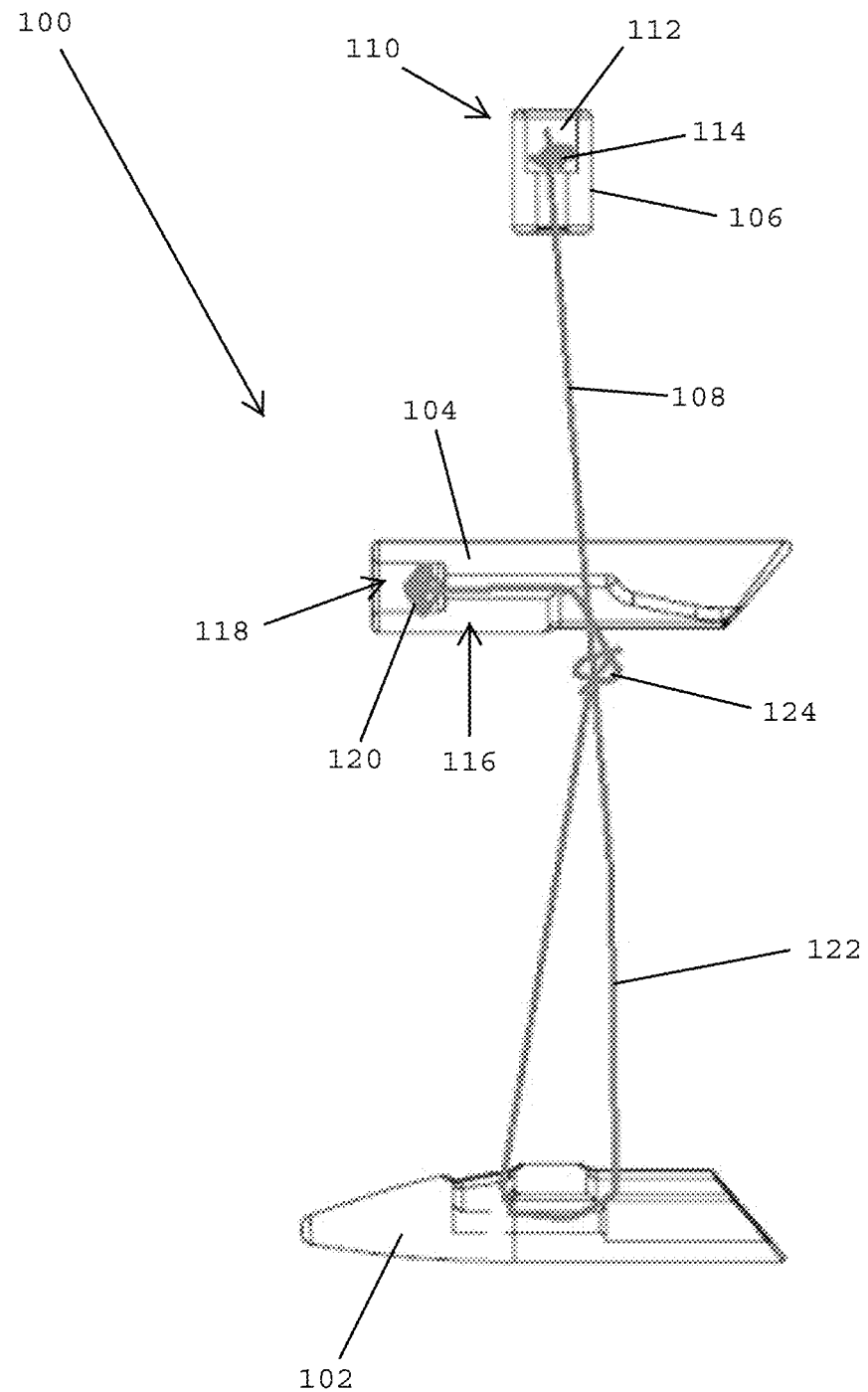
FIG. 1 shows a suture implant including a tissue anchor, a pledget, a tensioner and suture material, in accordance with one embodiment of the present patent application.

Referring to FIG. 1, in one embodiment, a suture implant 100 used in surgical procedures preferably includes a tissue anchor 102, a pledget 104, and a tensioner 106. The suture implant 100 preferably includes a suture 108 having a first end 110 that is secured within a recess 112 of the tensioner 106 via a knot 114 tied at the first end 110 of the suture. The suture 108 desirably includes a second end 116 that is disposed within a recess 118 formed in the pledget 104. The second end 116 of the suture 108 is secured to the pledget 104 via a knot 120 tied at the second end 116 and disposed within the recess 118 of the pledget.

In one embodiment, the suture 108 includes a suture loop 122 that extends between the pledget 104 and the tissue anchor 102. The suture includes a slip knot 124 positioned between the pledget 104 and the tissue anchor 102 that allows the pledget 104 to slide toward the tissue anchor 102 as tension is applied to the suture 108 via the tensioner 106. As used herein, the term "slip knot" means a knot that is made by tying the end of a suture around the suture itself to form a loop so that the size of the loop may be changed by slipping the knot In one embodiment, as the tensioner 106 is pulled away from the tissue anchor 102, the pledget 104 moves toward the tissue anchor 102 for applying a clamping force between an underside of the pledget and a top side of the tissue anchor. In one embodiment, the pledget and the tissue anchor are capable of toggling relative to one another so that major surfaces of the pledget and the tissue anchor oppose major surfaces of tissue and/or prosthetic implants.

In one embodiment, the tissue anchor 102, the pledget 104, and/or the tensioner 106 may be made of absorbable and/or non-absorbable materials. Preferred absorbable materials may include PDS, PDS/lactide-glycolide blends, PLA, etc. In one embodiment, each suture implant is sized to fit inside of a 5 mm outer diameter tube (typically trocar cannula dimension). The tissue anchor, the pledget and/or the tensioner may be fabricated by molding, however, with small modifications, other processes such as casting, stamping, and machining may be used. In one embodiment, the tissue anchor, the pledget and/or the tensioner may be extruded into a general shape, and then formed. In one embodiment, the tissue anchor, the pledget and/or the tensioner may be printed using a 3-D printer.

In one embodiment the suture 108 may be made of conventional, biocompatible, absorbable materials, non-absorbable materials, and combinations of absorbable and non-absorbable materials. Preferred non-absorbable materials include polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials include polydioxanone, polyglactin, polyglycolic acid, copolymers of glycolide and lactide, polyoxaesters, and poliglecaprone. In certain preferred embodiments, the suture 108 may include combinations of both absorbable and non-absorbable materials. In addition, metals or ceramics may be suitable for certain applications, such as instances where specific strength or corrosion resistance is necessary. In one preferred embodiment, the suture material preferably includes a polymer blend of polyvinylidene fluoride and polyvinylidene fluoride-co-hexafluoropropylene material. In addition, any of these materials may have conventional surface modifications that include coatings, plasma treatments, therapeutics, and the like. In one embodiment, the suture 108 is a polypropylene suture sold under the trademark PROLENE® by Ethicon, Inc of Somerville, N.J.

Figure 2:
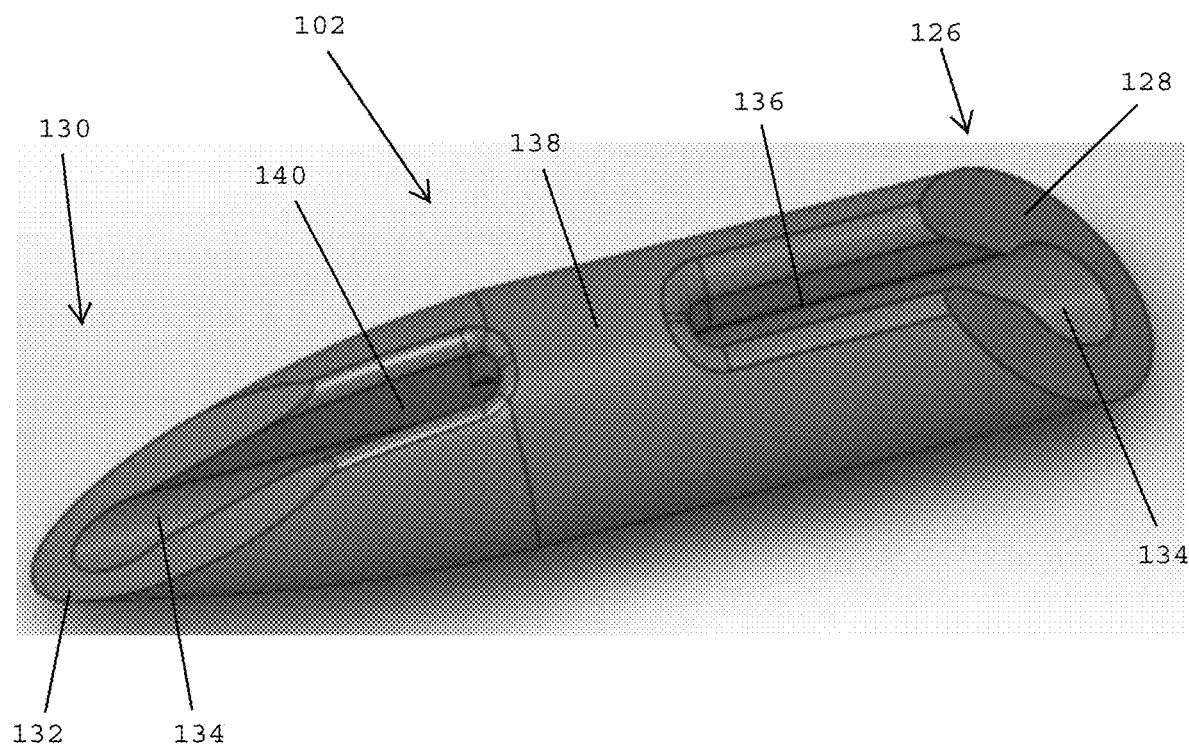
FIGS. 2 and 3 show the tissue anchor of FIG. 1.

Referring to FIG. 2, in one embodiment, the tissue anchor 102 includes a proximal end 126 having an angled face 128 and a distal end 130 defining a pointed end 132. In one embodiment, the tissue anchor 102 includes an elongated conduit 134 that extends from the proximal end 126 to the distal end 130 of the tissue anchor. The tissue anchor 102 preferably includes a trailing elongated slot 136 that extends from the angled face 128 to a mid-section 138 and a leading elongated slot 140 that extends from the mid-point 138 to the distal end 130 of the tissue anchor 102. In one embodiment, the mid-point 138 defines a closed surface at a top side of the tissue anchor, which is bounded on either side by openings for the suture loop 122 (FIG. 1).

Figure 3:
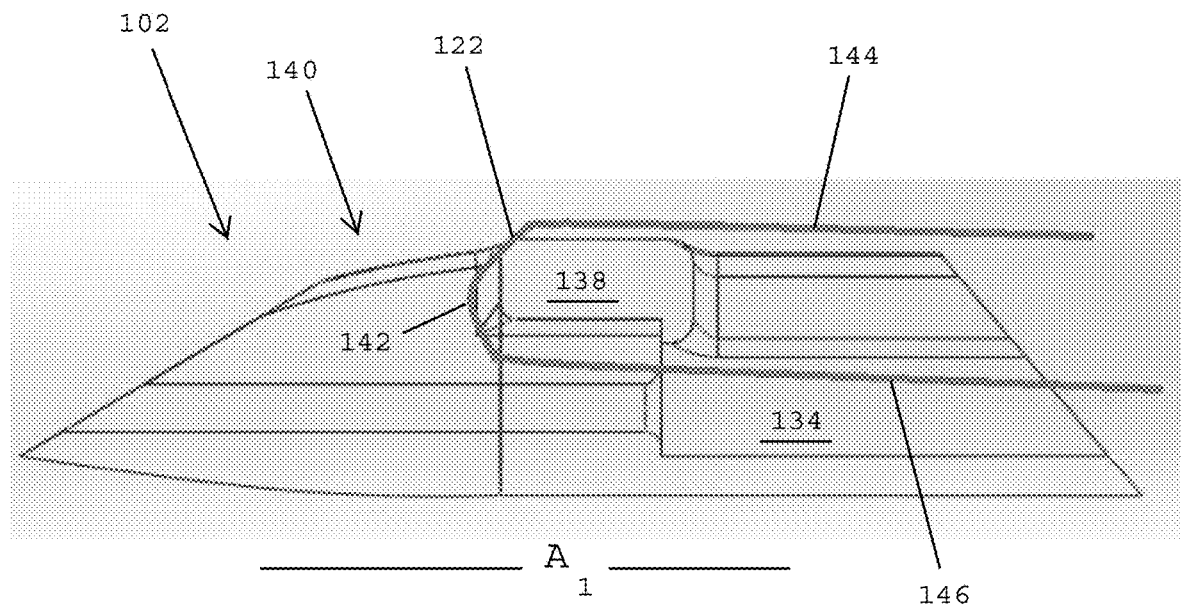

Referring to FIG. 3, in one embodiment, the suture loop 122 has a closed end 142 that is wrapped around the midsection 138 of the tissue anchor 102. In one embodiment, before deployment of the suture implant 100 (FIG. 1) from a delivery device, the first strand 144 of the suture loop 122 desirably passes over the top of the mid-section 138, the closed end 142 of the suture loop 122 extends through the leading elongated slot 140 of the tissue anchor 102, and a second strand 146 of the suture loop 122 passes through the elongated conduit 134. In one embodiment, prior to deployment of the tissue anchor 102, the first and second strands 144, 146 extend along the longitudinal axis $A_1$ of the tissue anchor. After deployment of the tissue anchor 102 into tissue, the orientation of the longitudinal axis of the tissue anchor relative to the suture loop 122 may change to the orientation shown in FIG. 1, which may be orthoganol to the longitudinal axis $A_1$ of the tissue anchor.

Figure 4:
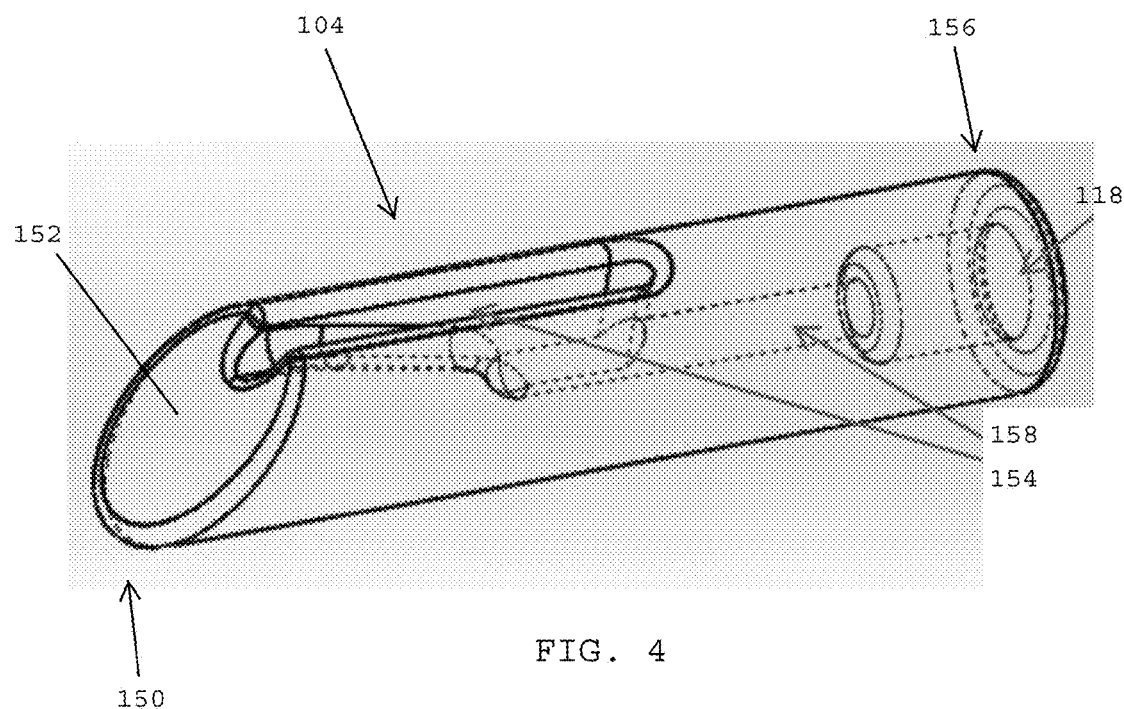
FIG. 4 shows the pledget of FIG. 1.

Referring to FIG. 4, in one embodiment, the pledget 104 includes a first end 150 having an angled face 152. The pledget 104 desirably includes an elongated slot 154 that extends from a mid-point of the pledget to the angled face 152 of the pledget. In one embodiment, the pledget includes a second end 156 having the recess 118 formed therein for receiving the knot 120 at the second end 116 of the suture 108 (FIG. 1). In one embodiment, the pledget 104 includes an elongated conduit 158 that extends from the recess 118 to the elongated slot 154. As will be described in more detail, in one embodiment, the suture material preferably is disposed within the elongated slot 154 prior to deployment of the suture implant. In one embodiment, the slip knot 124 (FIG. 1) of the suture is positioned within the elongated slot 154 to prevent the slip knot from contacting tissue, which may cause irritation or pain for a patient.

Figure 5A:
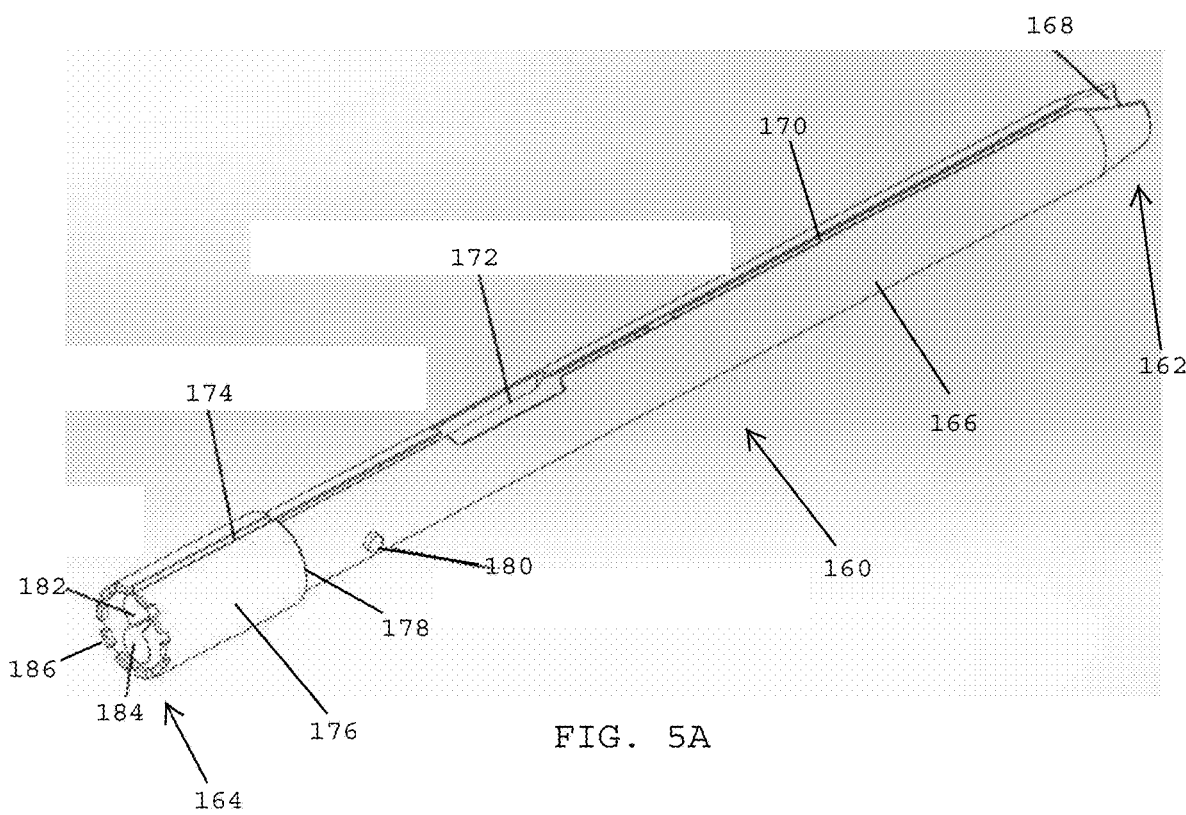
FIGS. 5A and 5B show a cartridge adapted to receive the suture implant of FIG. 1.

Referring FIG. 5A, in one embodiment, the suture implant 100 shown in FIG. 1 is loaded into a cartridge 160 used to deploy the suture implant during a surgical procedure. In one embodiment, the cartridge 160 has a proximal end 162, a distal end 164, and a tube shaped body 166 that extends between the proximal and distal ends 162, 164. In one embodiment, the cartridge 160 includes a tensioner channel 168 for inserting the tensioner 106 (FIG. 1) into the cartridge, a proximal suture slot 170 that extends from the tensioner channel toward the distal end 164 of the cartridge 160, a pledget opening 172 located at the distal end of the proximal suture slot 170 for inserting the pledget 104 (FIG. 1) into the cartridge 160, and a distal suture slot 174 that extends from the pledget opening 172 and the distal end 164 of the cartridge 160. In one embodiment, the pledget opening 172 is wider than the width of the proximal and distal suture slots 170, 174. In one embodiment, the cartridge 160 includes an end cap 176 having a slightly larger outer diameter than the outer diameter of the cartridge body 166. The larger diameter end cap 176 defines a stop 178 at a proximal end thereof that abuts against the distal end of an elongated shaft of a delivery device as will be described in more detail herein. In one embodiment, the cartridge 160 preferably includes locking pins 180 that are adapted to engage with the elongated shaft of the insertion tool for securing the cartridge 160 within the elongated shaft of the insertion tool.

In one embodiment, the end cap 176 preferably includes an upper channel 182 for dispensing the pledget 104 (FIG. 1) from the distal end of the end cap and a lower channel 184 for dispensing the tissue anchor 102 (FIG. 1) from the distal end of the end cap.

Figure 5B:
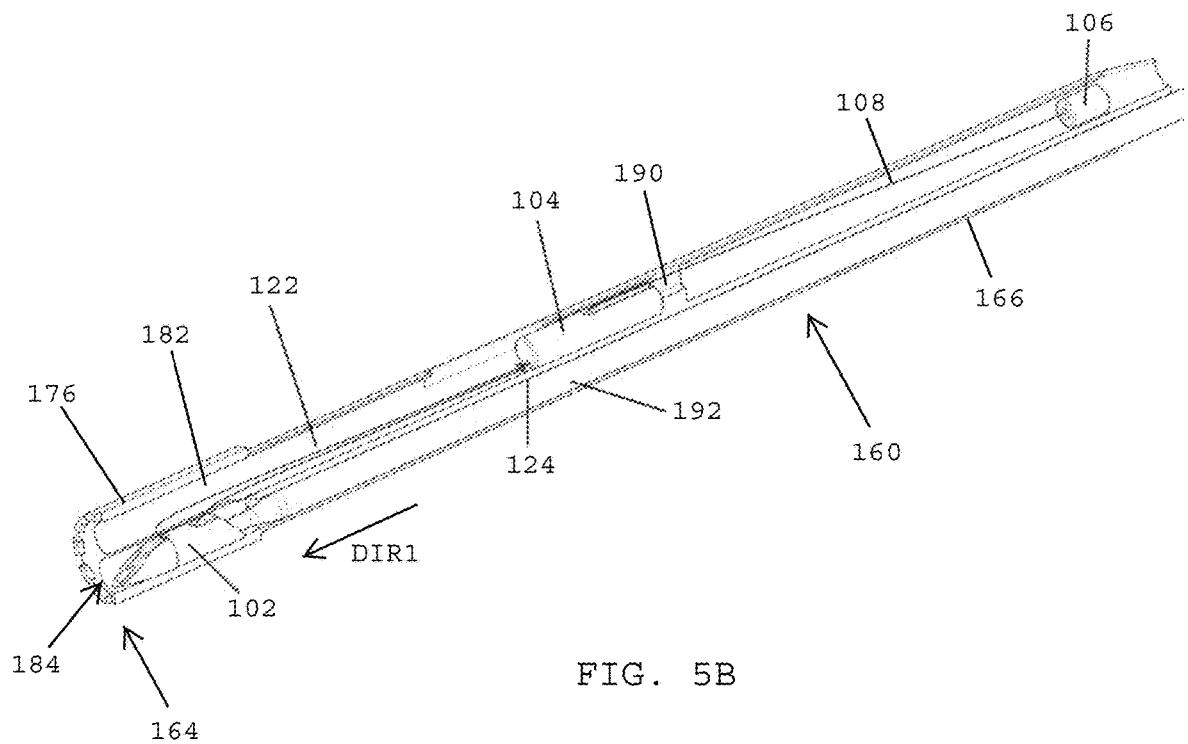

Referring to FIGS. 5A and 5B, in one embodiment, the tissue anchor 102 is inserted into the lower channel 108 of the end cap 176 and the suture loop 122, which is connected to the tissue anchor, is passed through the distal suture slot 174. The pledget 104 is desirably inserted into the relatively wider pledget opening 172 and the suture material extending between the pledget 104 and the tensioner 106 is passed through the proximal suture slot 170. The tensioner 106 is preferably inserted into the tensioner channel 168 at the proximal end 162 of the cartridge 160.

Referring to FIG. 5B, in one embodiment, the cartridge 160 preferably includes the upper channel 182 that extends to the distal end of the end cap 176. The upper channel 182 receives the pledget 104 and the suture loop 122 that extends between the pledget 104 and the tissue anchor 102. The tissue anchor 102 is positioned within the lower channel 184. The slip knot 124 (FIG. 1) is disposed within the upper channel 182 and is preferably located between the pledget 104 and the tissue anchor 102. A proximal end of the suture material 108 preferably extends between the pledget 104 and the tensioner 106. The cartridge body 166 desirably includes a hard stop 190 that is disposed between a proximal end of the pledget 104 and the tensioner 106.

In one embodiment, a delivery device desirably has a tissue anchor driver 192 that is disposed within the second channel 184 of the cartridge 160. In one embodiment, the insertion tool may be engaged for advancing the tissue anchor driver 192 in a distal direction designated DIR1 for dispensing the tissue anchor 102 from the second channel 184 at the distal end 164 of the cartridge 160.

Figure 6:
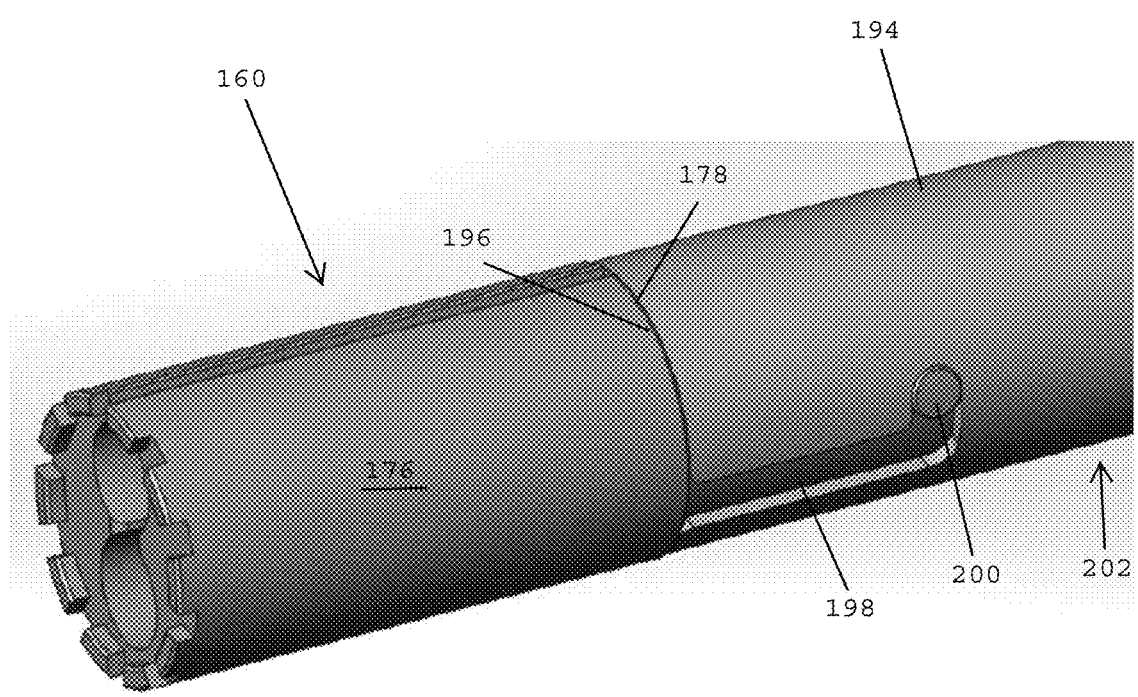
FIG. 6 shows the cartridge of FIGS. 5A and 5B secured to a distal end of an elongated shaft of an applicator instrument, in accordance with one embodiment of the present patent application.

Referring to FIG. 6, in one embodiment, the cartridge 160 is secured to a distal end of an elongated shaft 194 of a delivery device. In one embodiment, the elongated shaft 194 has a distal end 196 with a pair of L-shaped slots having open ends at the distal end 196 of the elongated shaft 194 of the delivery device. The locking pins 180 (FIG. 5A) projecting from opposite sides of the cartridge body are desirably inserted into the open ends of the L-shaped slots 198 for securing the cartridge 160 to the elongated shaft 194. The body 166 (FIG. 5A) of the cartridge 160 slides into the larger diameter elongated shaft 194. The proximal end 178 of the larger diameter end cap 176 of the cartridge 160 abuts against the distal edge 196 of the elongated shaft 194 for halting further insertion of the cartridge 160 into the elongated shaft 194. During insertion of the cartridge 160 into the elongated shaft 194, the locking pins 180 preferably abut against the closed ends of the L-shaped slots 198 for halting further insertion of the cartridge 160 into the elongated shaft 194 of the insertion tool. The cartridge may be rotate ¼ turn to secure the cartridge to the distal end of the elongated shaft 194 of the delivery device 202.

Figure 7A:
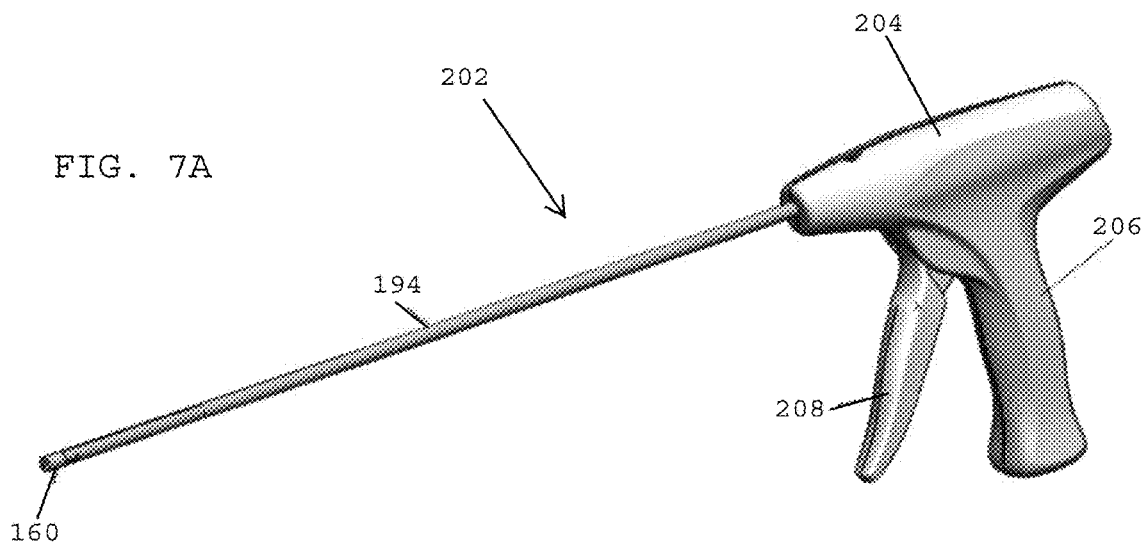
FIGS. 7A-7C show an applicator instrument having the cartridge of FIGS. 5A-5B and 6 secured to a distal end of an elongated shaft, in accordance with one embodiment of the present patent application.
Figure 7B:
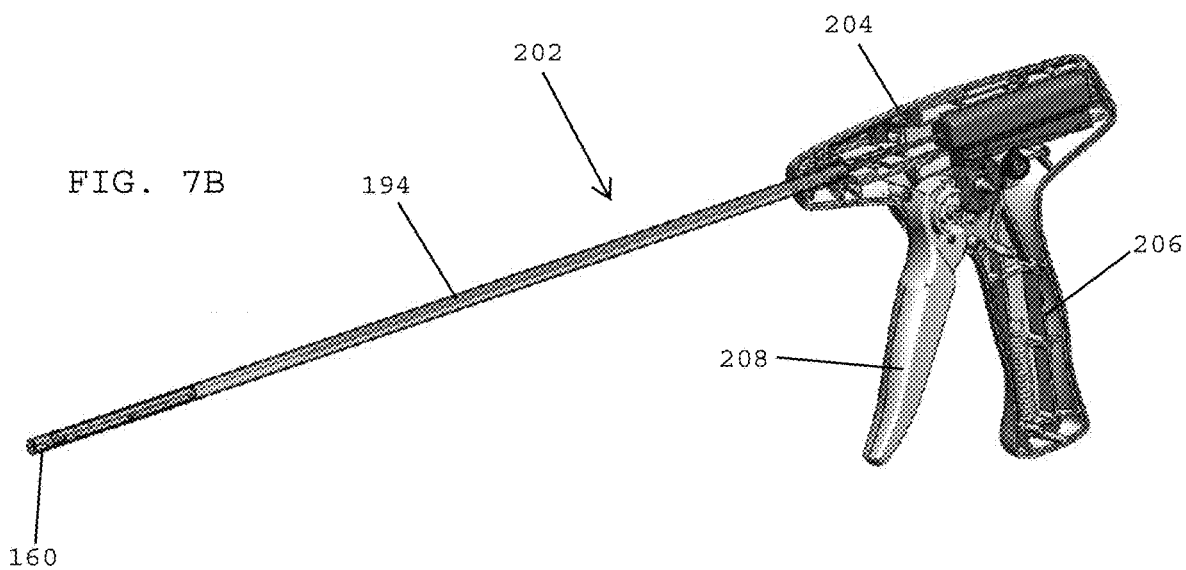

Referring to FIGS. 7A and 7B, in one embodiment, a delivery device 202 is adapted to receive the cartridge 160 (having the suture implant loaded therein) for dispensing the suture implant 100 (FIG. 1) from the distal end of the elongated shaft 194. In one embodiment, the insertion tool 202 preferably includes a housing 204, a handle 206, and a trigger 208 that may be squeezed for dispensing the suture implant from the distal end of the elongated shaft 194.

Figure 7C:
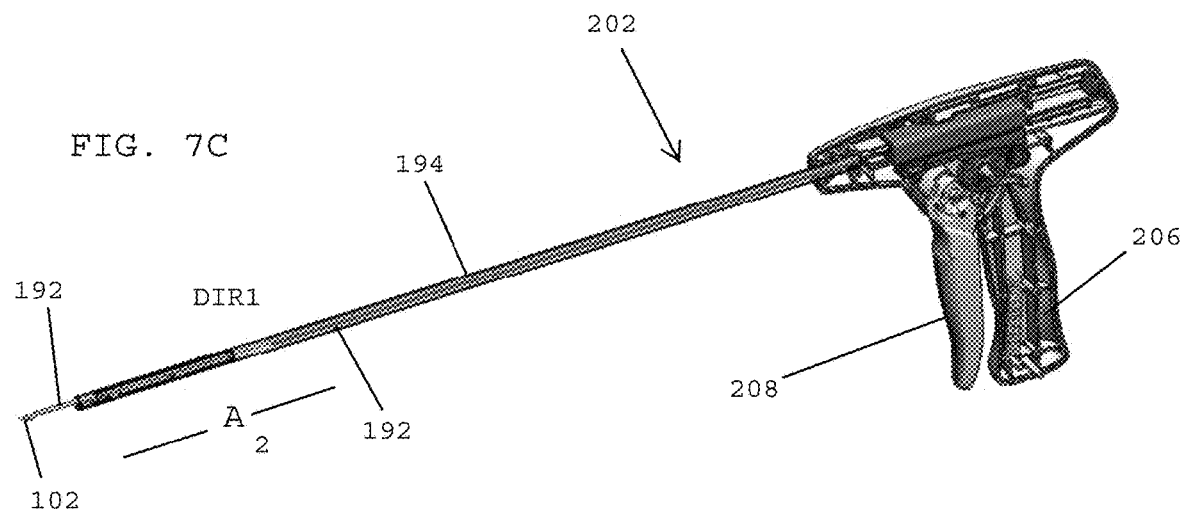

Referring to FIG. 7C, in one embodiment, when the trigger 208 is squeezed toward the handle 206, the firing system of the insertion tool 202 moves the anchor driver 192 (FIG. 5B) in the distal direction DIR1 along the axis $A_2$ for dispensing the tissue anchor 102 from the distal end of the elongated shaft 194.

Figure 8A:
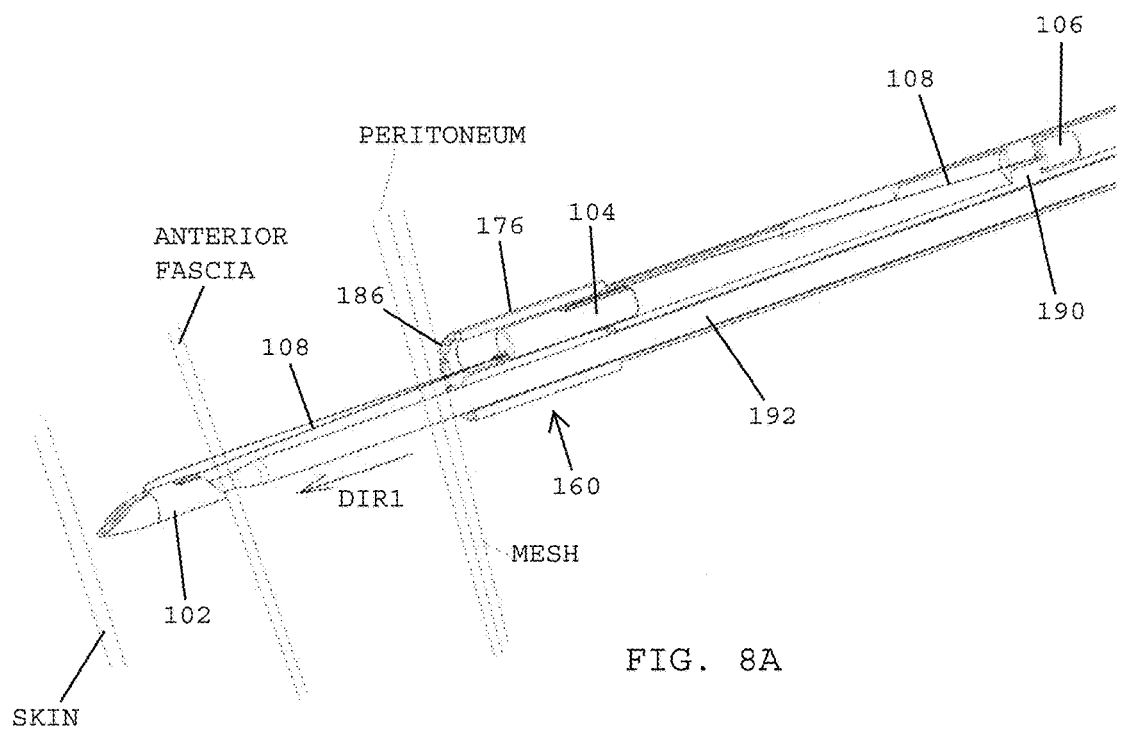
FIGS. 8A-8C show a method of using the applicator instrument of FIGS. 7A-7C for implanting the suture implant of FIG. 1, in accordance with one embodiment of the present patent application.

Referring to FIG. 8A, in one embodiment, during a hernia repair procedure, a surgical mesh is positioned over the peritoneum of a patient. The projections 186 at the distal end of the end cap 176 of the cartridge 160 (FIG. 5A) are abutted against the mesh to hold the mesh in place. The trigger of the insertion tool 202 (FIGS. 7A-7C) is squeezed for moving the tissue anchor driver 192 in the distal direction designated DIR1. As the tissue anchor driver 192 moves distally, the distal end of the tissue anchor driver 192 pushes the tissue anchor 102 from the distal end of the cartridge 160 for deploying the tissue anchor 102 into tissue. As the tissue anchor advances into the tissue, the suture material 108, which is connected with the pledget 104 and the tensioner 106, drags the pledget 104 and the tensioner 106 in the distal direction DIR1.

Figure 8B:
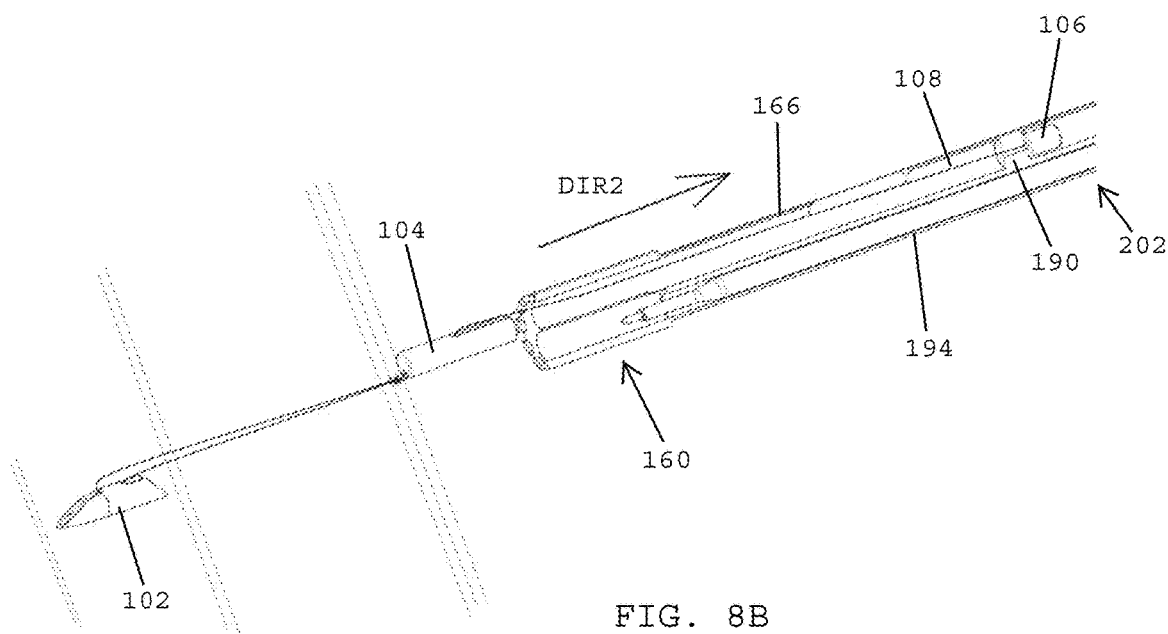

Referring to FIG. 8B, in one embodiment, after the tissue anchor 102 is deployed between the anterior fascia and the skin, the elongated shaft 194 of the insertion tool 202 is retracted in the direction designated DIR2. At this stage, the pledget 104 is fully deployed from the insertion tool and is disposed within tissue. At this stage, further distal deployment of the tensioner 106 is stopped. As the elongated shaft 194 is retracted in the direction DIR2, the stop 190 moves the tensioner 106 in the direction DIR2 which applies tension to the suture material 108 extending between the tissue anchor 102 and the stop 190.

Figure 8C:
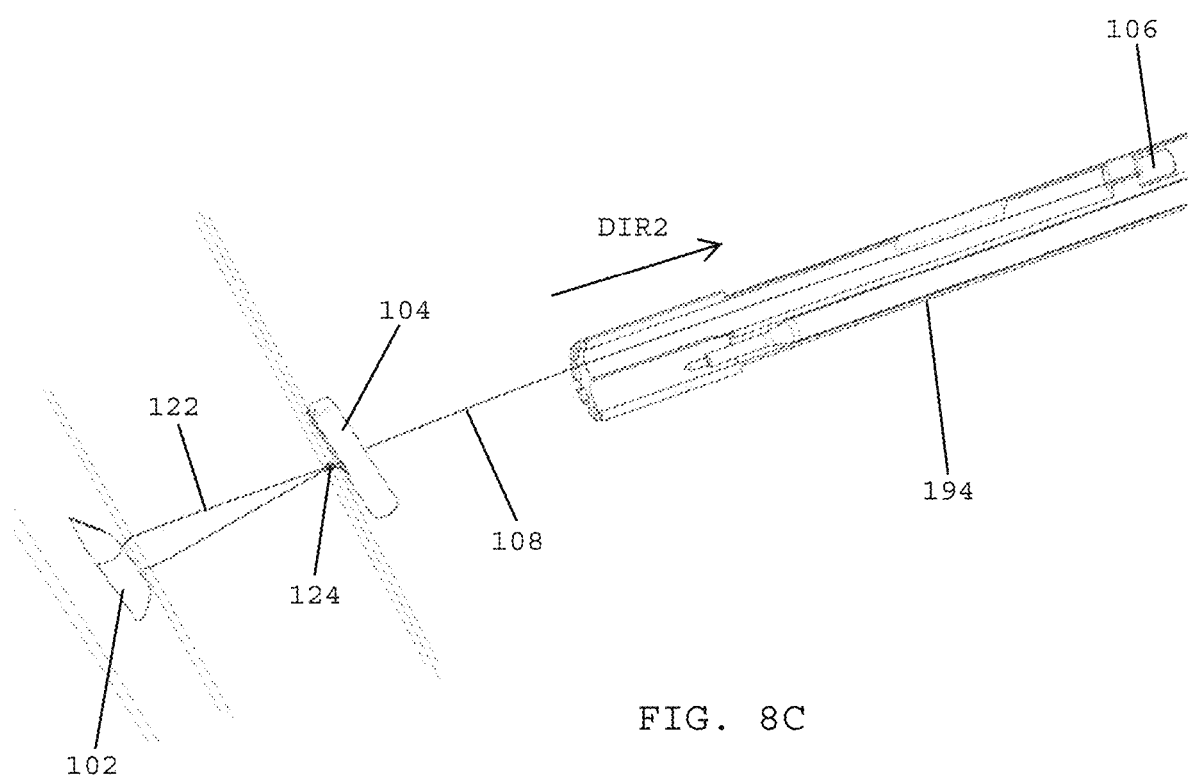

Referring to FIG. 8C, in one embodiment, further movement of the elongated shaft 194 in the direction DIR2 moves the tensioner 106 in the direction DIR2, which reduces the distance between the pledget 104 and the tissue anchor 102 by shortening the suture loop 122 by sliding the slip knot 124. As tension is applied to the suture 108 by the tensioner 106, the distance between the pledget 104 and the tissue anchor 102 is reduced for applying a compressing or clamping force between the pledget and the tissue anchor. As tension of applied to the suture material 108, the pledget 104 and the tissue anchor 102 may toggle between the positions shown in FIG. 8B to the positions shown in FIG. 8C for securing the mesh to the peritoneum. In FIG. 8B, the tissue anchor 102 and the pledget 104 are in a deployment configuration whereby the respective longitudinal axes of the tissue anchor and the pledget are aligned with the longitudinal axis $A_2$ of the elongated shaft 194. In FIG. 8C, the tissue anchor 102 and the pledget 104 are in a clamping configuration whereby the respective longitudinal axes of the tissue anchor and the pledget are orthogonal (e.g., perpendicular) with the longitudinal axis $A_2$ of the elongated shaft 194.

Figure 9:
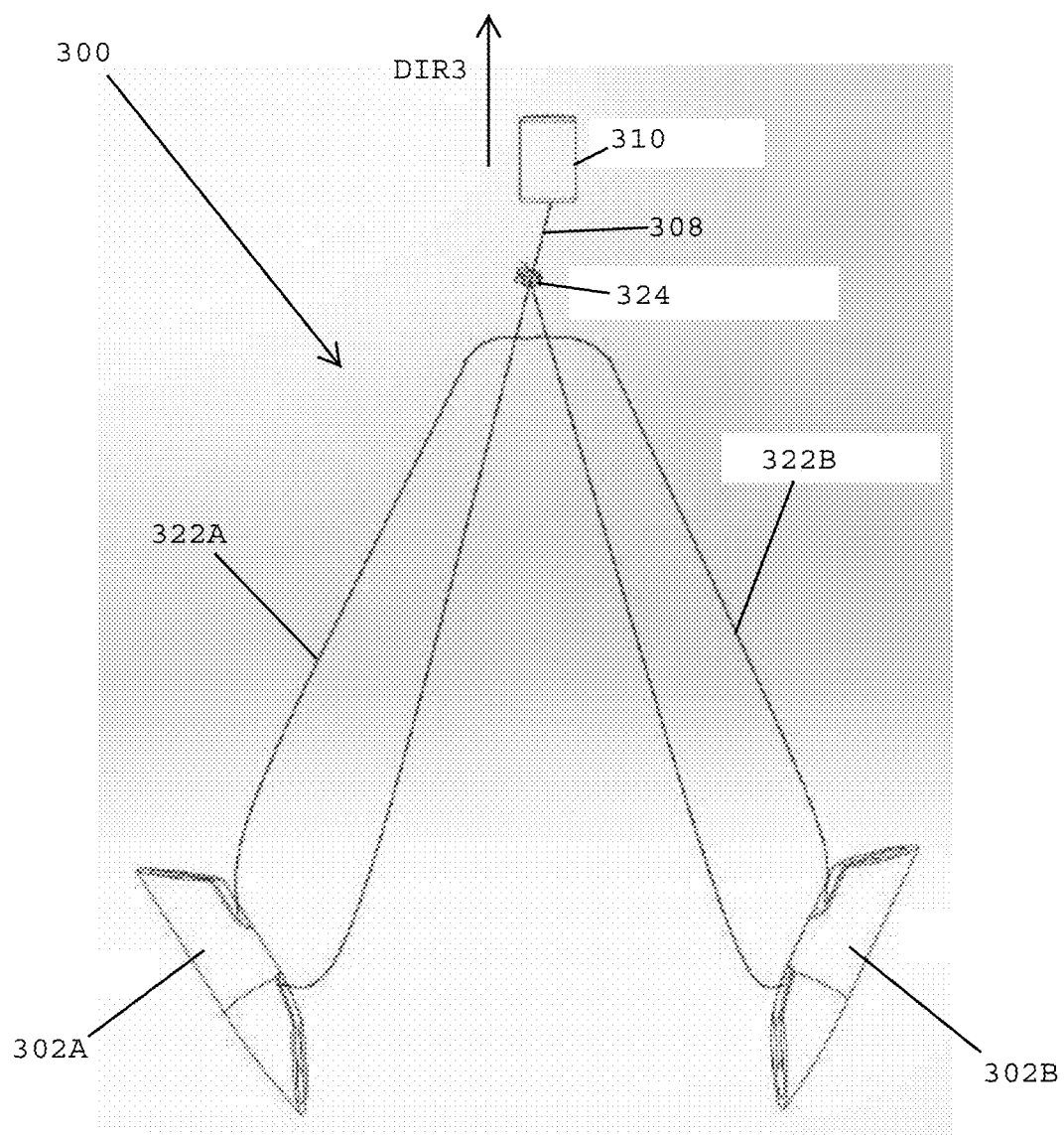
FIG. 9 shows a suture implant, in accordance with one embodiment of the present patent application.

Referring to FIG. 9, in one embodiment, a suture implant 300 preferably includes a first tissue anchor 302A and a second tissue anchor 302B. In one embodiment, the first and second tissue anchors 302A, 302B are similar to the tissue anchor 102 described above in the embodiment shown in FIG. 1.

In one embodiment, the suture implant 300 desirably includes an elongated suture 308 having a first end secured to a tensioner 310. The suture 308 preferably includes a first suture loop 322A that passes through the first tissue anchor 302A, and a second suture loop 322B that passes through the second tissue anchor 302B. The suture implant 300 also desirably includes a slip knot 324 that is in communication with the first and second suture loops 322A, 322B. In one embodiment, as the tensioner 310 is pulled away from the first and second tissue anchors 302A, 302B in the direction indicated DIR3, the slip knot 324 moves toward the first and second tissue anchors 302A, 302B for reducing the distance between the slip knot and the respective tissue anchors 302A, 302B.

Figure 10A:
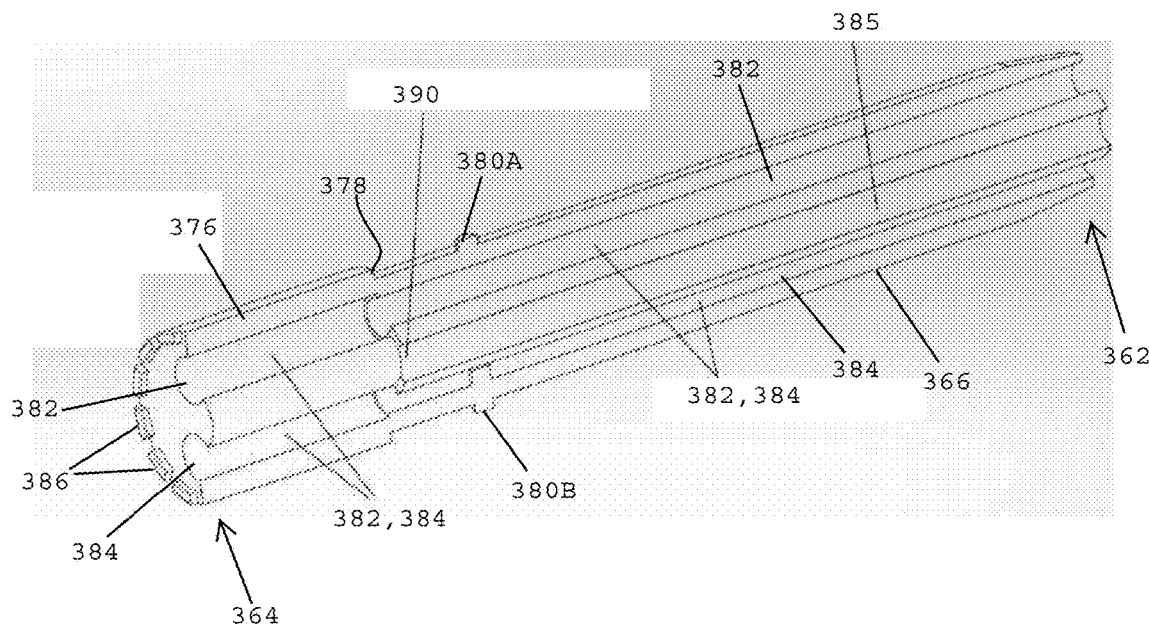
FIGS. 10A-10B show a cartridge for the suture implant of FIG. 9, in accordance with one embodiment of the present patent application.
Figure 10B:
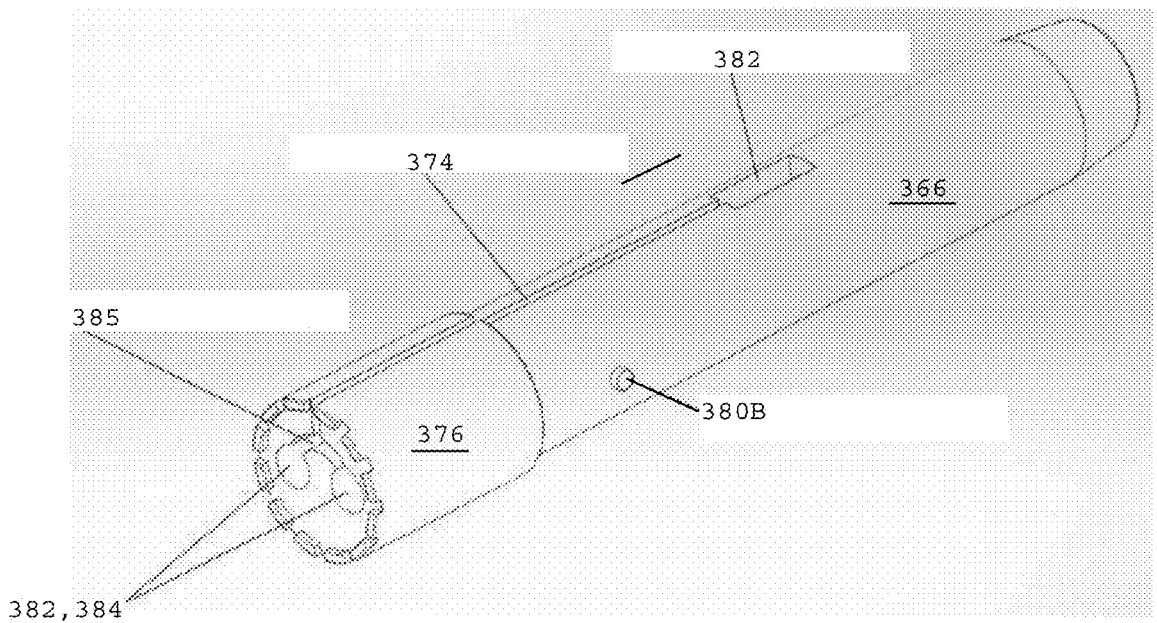

Referring to FIGS. 9, 10A, and 10B, in one embodiment, the suture implant 300 is positioned within a suture implant cartridge 360. Referring to FIG. 10A, in one embodiment, the cartridge 360 preferably has a proximal end 362 a distal end 364. The cartridge 360 desirably includes a cartridge body 366 having a substantially cylindrical shape that extends from the proximal end 362 of the cartridge 360 to an end cap 376 located adjacent the distal end 364 of the cartridge 360. In one embodiment, a proximal end of the cartridge is insertable into a distal end of an elongated shaft of a delivery device.

In one embodiment, the cartridge body 366 desirably has a first driver channel 382 that extends from the proximal end 362 to the distal end 364 of the cartridge 360, and a second driver channel 384 that extends from the proximal end 362 to the distal end 364 of the cartridge 360. In one embodiment, the two driver channels are parallel to one another.

In one embodiment, the cartridge 360 desirably includes a pair of alignment pins 380A, 380B projecting from opposite sides, that are utilized for aligning and securing the cartridge 360 to a distal end of an elongated shaft of a delivery device. In one embodiment, the cartridge 360 preferably has a stopper 390 that is adapted to engage a distal end of the tensioner 310 (FIG. 9) for applying tension to the suture material. In one embodiment, the end cap 376 desirably includes projections 386 extending from a distal-most end of the end cap 376 for engaging a surgical mesh surface to stabilize the surgical mesh over tissue during a suture implant insertion step. In one embodiment, the end cap 376 has an outer diameter that is larger than the outer diameter of the cylindrical-shaped body 366 of the cartridge 360. The larger relative outer diameter of the end cap 376 defines an end cap stop 378 that desirably abuts against a distal-most end of an elongated shaft of a delivery device for halting insertion of the cartridge 360 into the distal end of the elongated shaft of the insertion tool.

In one embodiment, the first and second driver channels 382, 384 extend to the distal end face of the end cap 376 so that the first and second tissue anchors 302A, 302B (FIG. 9) may be dispensed from the end cap 376 of the cartridge 360.

Referring to FIG. 10B, in one embodiment, the first and second driver channels 382, 384 extend to the distal end face of the end cap 376. The end cap 376 also desirably includes a suture loop channel 385 that interconnects upper ends of the first and second drive channels 382, 384. During tensioning of the suture implant 300 described above in FIG. 9, the first and second suture loops 322A, 322B and the slip knot 324 may pass through the suture loop channel 385.

In one embodiment, the cartridge 360 preferably includes a suture slot 374 for inserting the suture material into the body 366 of the cartridge 360. In one embodiment, the cartridge 360 also desirably includes a tensioner opening 372 for inserting the tensioner 310 (FIG. 9) into the body 366 of the cartridge 360. In one embodiment, the tensioner opening 372 is wider than the suture slot 374.

In one embodiment, the locking pin 380B projects laterally from the side of the cartridge body 366. The locking pin 380B preferably engages a slot at a distal-most end of an elongated shaft for securing the cartridge 360 within the distal end of the elongated shaft.

In one embodiment, the cartridge body 366 desirably includes a tensioner channel 385 that is adapted to receive the tensioner 310 (FIG. 9) and allow distal movement of the tensioner within the tensioner channel 385 until it abuts against a proximal end of the tensioner stopper 390 of the end cap 376.

Figure 11A:
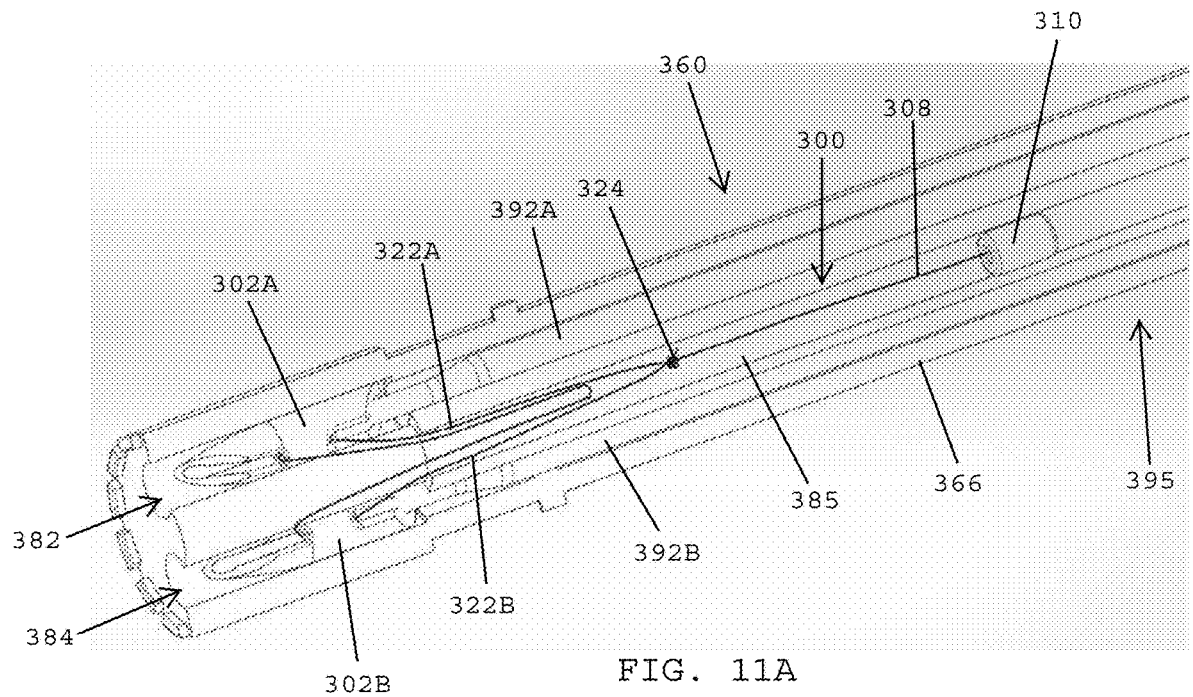
FIGS. 11A-11C show a method of utilizing the cartridge of FIGS. 10A and 10B for implanting the suture implant of FIG. 9, in accordance with one embodiment of the present patent application.

Referring to FIG. 11A, in one embodiment, the suture implant 300 is inserted into the cartridge body 366 with the first tissue anchor 302A disposed within the first driver channel 382 and the second tissue anchor 302B disposed within the second driver channel 384. In one embodiment, the slip knot 324 is disposed within the tensioner channel. The first suture loop 322 has a distal end coupled with the first tissue anchor 302A and a proximal end that is disposed within the tensioner channel 385. Similarly, the second suture loop 322B has a distal end coupled with the second tissue anchor 302B and a proximal end disposed within the tensioner channel 385. The tensioner 310 is desirably secured to the proximal end of the suture material 308 and is preferably disposed within the tensioner channel 385.

In one embodiment, a delivery device 395 preferably includes a first tissue anchor driver 392A having a distal end that is configured to engage the first tissue anchor 302A, and a second tissue anchor driver 392B having a distal end that is configured to engage the second tissue anchor 302B.

Figure 11B:
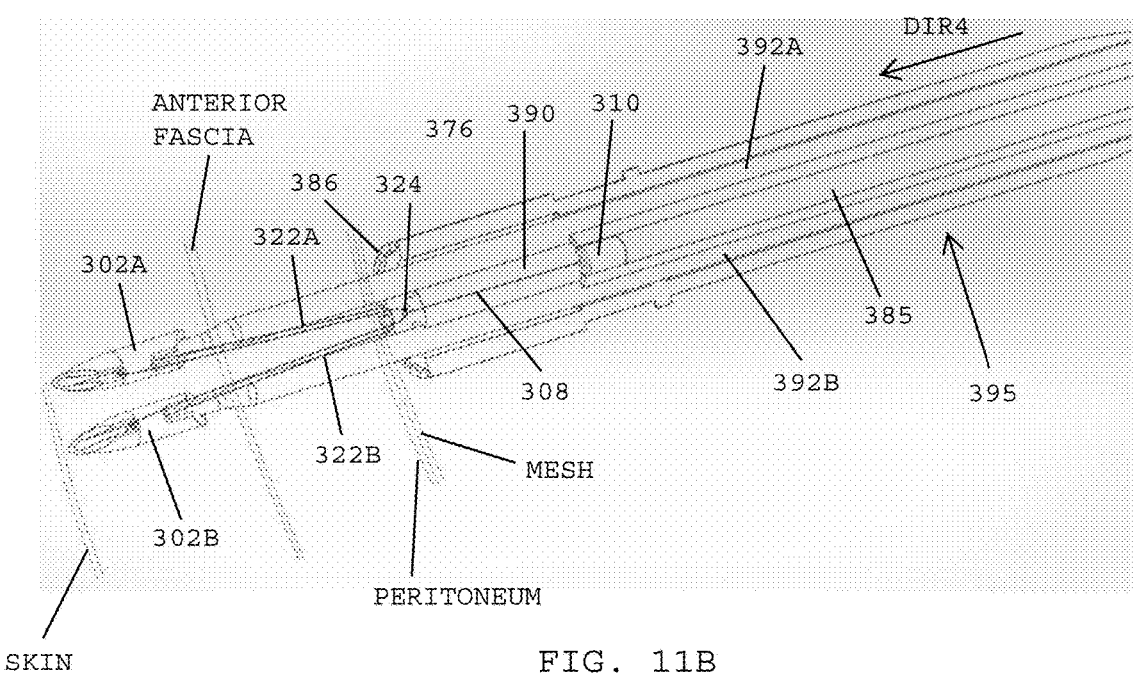

Referring to FIG. 11B, in one embodiment, a surgical mesh is secured to tissue by unfurling the mesh over the peritoneum of the patient. In one embodiment, an actuator or trigger on the insertion tool 395 is engaged for advancing the first and second tissue anchor drivers 392A, 392B from the distal end of the end cap 376. As the distal ends of the tissue anchor drivers 392A, 392B move in the direction DIR4, the tissue anchor drivers advance the first and second tissue anchors 302A, 302B through the mesh, the peritoneum, and into the anterior fascia, whereupon the first and second tissue anchors 302A, 302B are located under the skin. As the first and second tissue anchors 302A, 302B are advanced into the anterior fascia, the first and second suture loops 322A, 322B and the slip knot 324 are also preferably dispensed from the distal end of the end cap 376. In turn, the suture material 380 pulls the tensioner 310 through the tensioner channel 385 until a distal end of the tensioner 310 abuts against a proximal end of the tensioner stop 390 located inside the end cap 376.

Figure 11C:
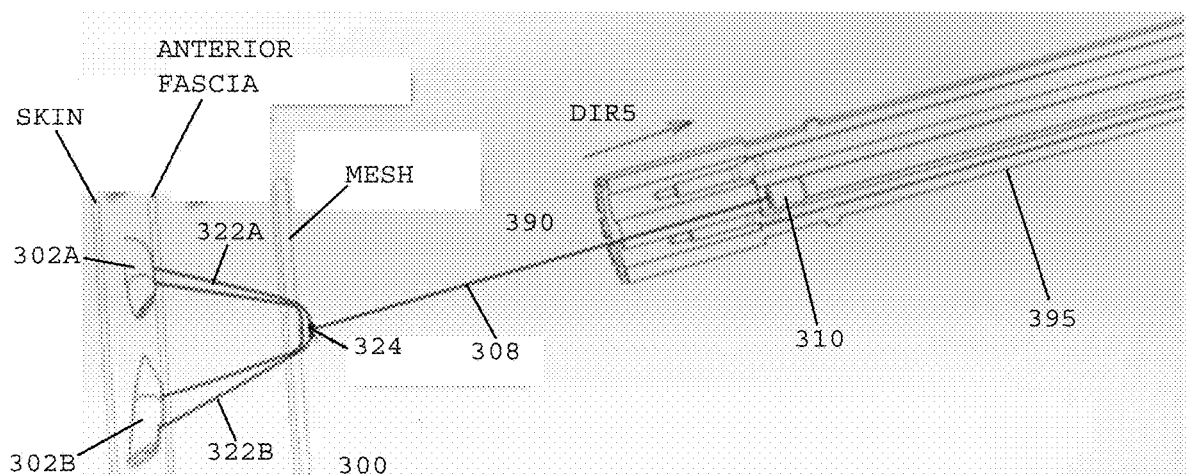

Referring to FIG. 11C, after the first and second tissue anchors 302A, 302B have been advanced into the anterior fascia layer, the first and second suture loops 322A, 322B desirably extend between the respective first and second tissue anchors 302A, 302B and the slip knot 324. In order to apply tension to the suture implant, the insertion tool 395 is preferably retracted in the direction DIR5. As the insertion tool 395 is retracted, the tensioner 310 abuts against the tensioner stop 390, which draws the slip knot 324 closer to the first and second tissue anchors 302A, 302B. As tension is applied to the suture implant, the first and second tissue anchors 302A, 302B are free to toggle relative to the boundary between the anterior fascia and the peritoneum to assume the orientation shown in FIG. 11C. In one embodiment, after appropriate tension levels have been applied to the first and second suture loops 324A, 324B, a free end of the suture material 308 may be cut for disconnecting the insertion tool 395 from the suture implant 300.

Figure 12:
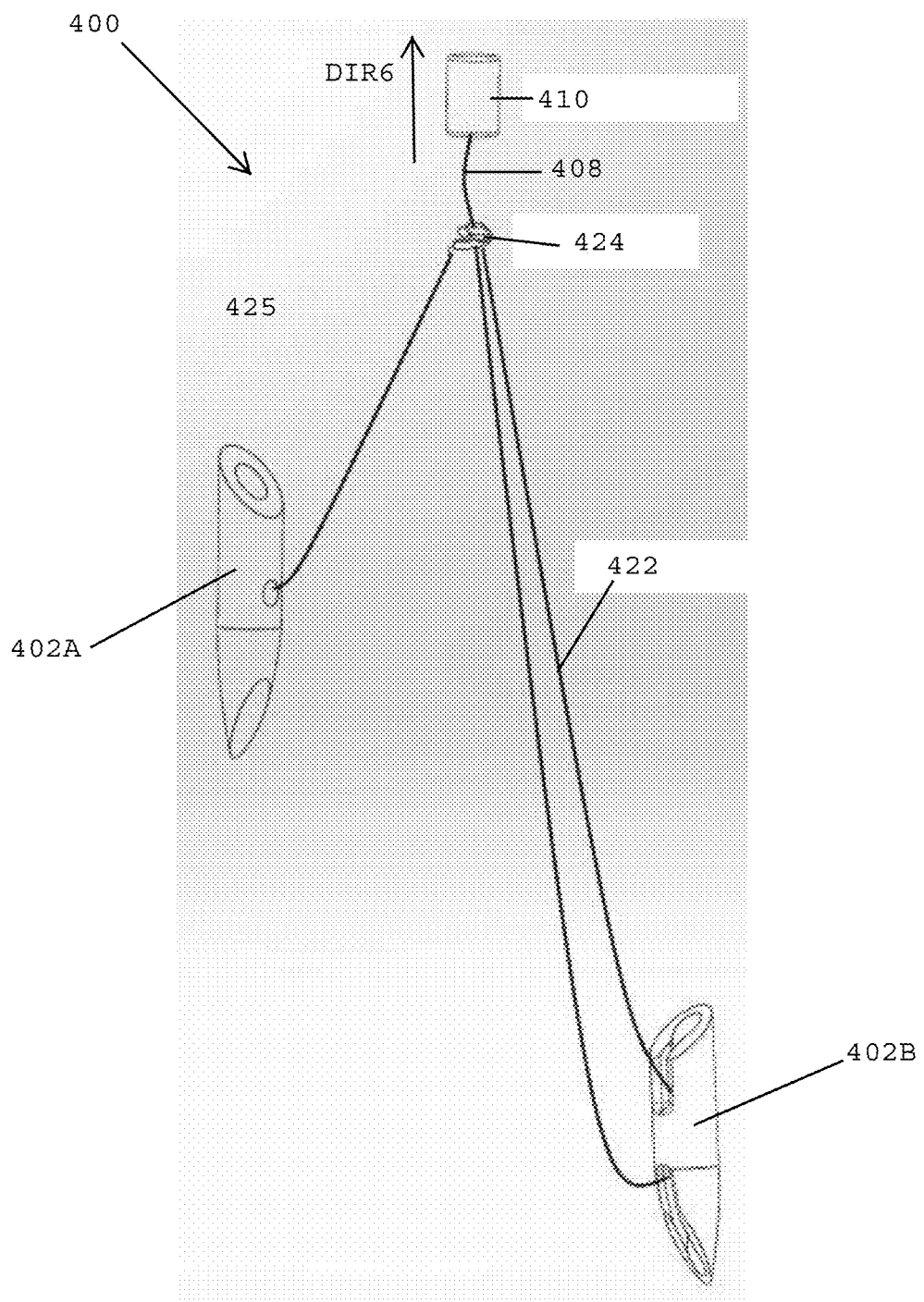
FIG. 12 shows a suture implant having a shallow tissue anchor and a deeper tissue anchor, in accordance with one embodiment of the present patent application.

Referring to FIG. 12, in one embodiment a suture implant 400 has a first tissue anchor 402A adapted to be implanted at a shallower depth within the tissue and a second tissue anchor 402B adapted to be implanted at a deeper depth within the tissue. In one embodiment, the suture implant 400 desirably includes suture material 408 that couples a tensioner 410 with the first and second tissue anchors 401A, 402B. In one embodiment, a single strand of suture (without a loop) 425 extends between the first tissue anchor 402A and slip knot 424. The suture implant 400 includes a suture loop 422 having a closed end that passes through the second tissue anchor 402B and a proximal end that is in communication with the slip knot 424. In one embodiment, as the tensioner 410 is pulled in the direction designated DIR6 (i.e., away from the tissue anchors 402A, 402B), the slip knot 424 desirably moves toward the first and second tissue anchors 402A, 402B.

Figure 13A:
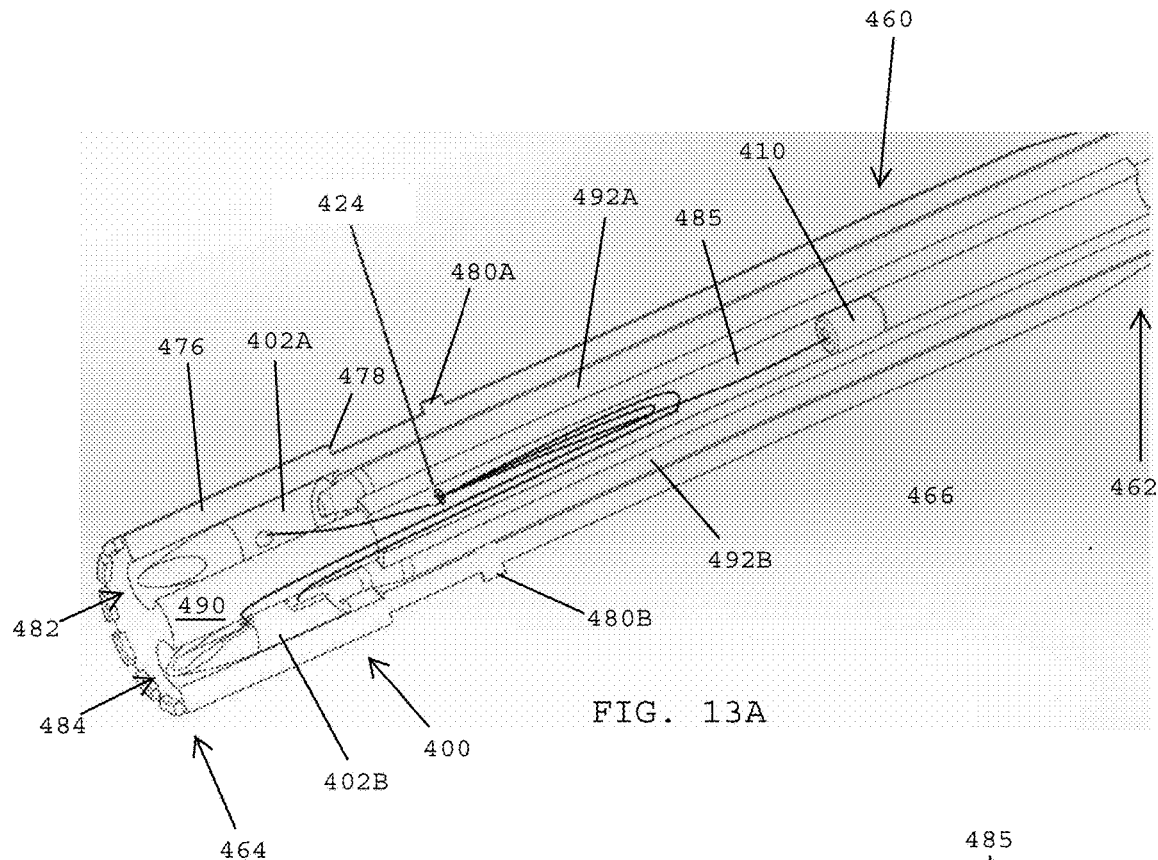
FIGS. 13A-13C show a method of using an applicator instrument for implanting the suture implant of FIG. 12 in tissue, in accordance with one embodiment of the present patent application.

Referring to FIG. 13A, in one embodiment, a cartridge 460 preferably includes a cylindrical-shaped cartridge body 466 that extends from a proximal end 462 to a distal end 464 of the cartridge 460. In one embodiment, the proximal end 462 of the cartridge body 466 is adapted to be inserted into a distal end of an elongated shaft of a delivery device. In one embodiment, the cartridge body 466 includes a pair of alignment pins 480A, 480B projecting from opposite sides thereof that enable the cartridge 460 to be secured to a distal end of an elongated shaft of a delivery device. In one embodiment, the cartridge 460 includes an end cap 476 having a slightly larger outer diameter than the outer diameter of the cylindrical-shaped cartridge body 466 to define an end cap stop 478 adapted to abut against the distal-most end of an elongated shaft of an applicator instrument.

In one embodiment, the cartridge body 466 preferably includes a first driver channel 482 adapted to receive a first tissue anchor driver 492A for the first tissue anchor 402A, and a second driver channel 484 adapted to receive a second tissue anchor driver 492B for engaging the second tissue anchor 402B.

In one embodiment, the cartridge 460 includes a stop 490 disposed within the end cap 476. The stop 490 preferably has a proximal end aligned with a central channel 485 that receives the tensioner 410 of the suture implant 400 (FIG. 12), a portion of the suture loop 422 and the slip knot 424.

In one embodiment, when the suture implant 400 is assembled into the cartridge 460, the first tissue anchor 402A is preferably disposed within the first channel 482 that extends through the end cap 476 and the cartridge body 466. The second tissue anchor 402B is preferably disposed within the second channel 484 that extends through the end cap 476 and the cartridge body 466. The slip knot 424 and the tensioner 410 are desirably disposed within the central channel 485. A single strand of suture material 425 preferably extends between the first tissue anchor 402A and the slip knot 424. The suture loop 422 desirably extends from the second tissue anchor 402B to the central channel 485 of the cartridge 460.

Figure 13B:
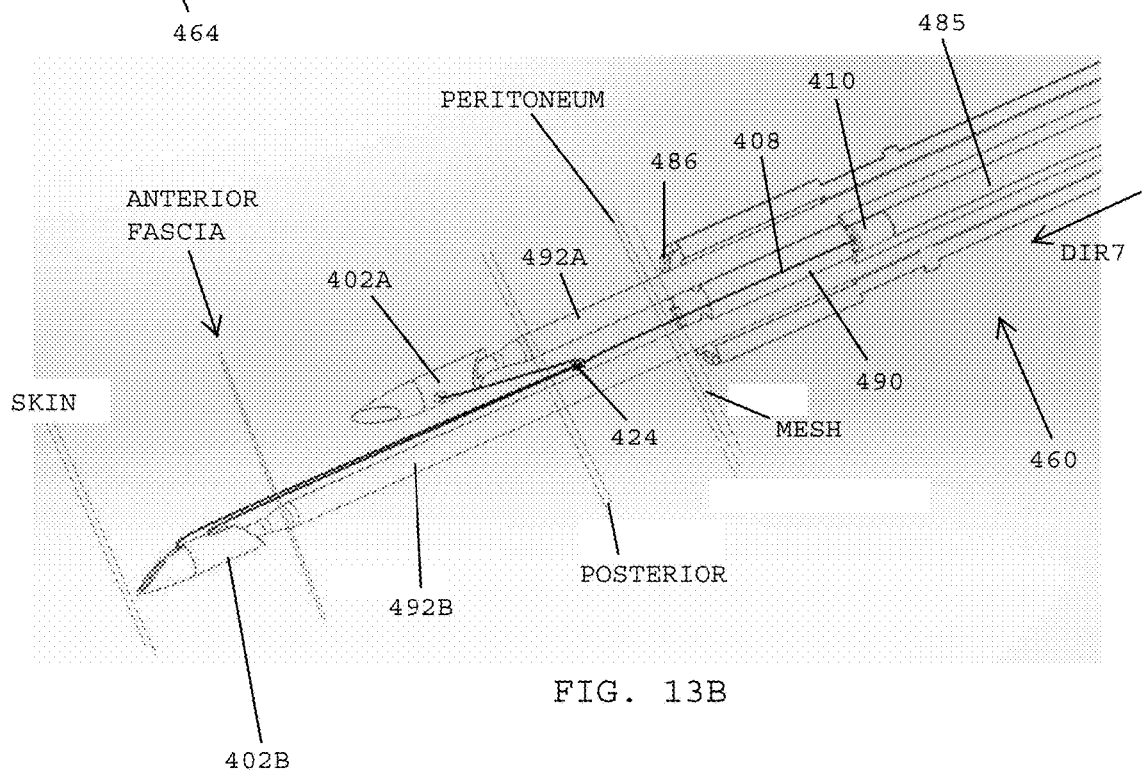

Referring to FIG. 13B, in one embodiment, the suture implant 400 is utilized for securing a surgical mesh over a peritoneum layer of a patient. In one embodiment, the surgical mesh is unfurled over the peritoneum layer. Projections 486 (e.g., castling) at a distal-most end of the end cap 476 of the cartridge 460 are desirably abutted against a posterior face of the surgical mesh for holding the surgical mesh in place over the peritoneum layer. An actuator or trigger on a delivery device instrument may be engaged (e.g., squeezed) for advancing the respective first and second tissue anchor drivers 392A, 392B in the direction designated DIR7. The second tissue anchor driver 392B desirably advances further than the first tissue anchor driver 392A so that the second tissue anchor 402B is disposed between the anterior face of the anterior fascia and the skin layer, and the first tissue anchor 402A is disposed between the anterior face of the anterior fascia and the posterior face of the anterior fascia. In one embodiment, the first and second tissue anchor drivers may advance distally at the same time. In one embodiment, the first and second tissue anchor drivers may advance distally at different times or at different rates, or distal advancement of one of the drivers may commence before distal advancement of the other driver. As shown in FIG. 13B, the first tissue anchor 402A is disposed at a shallower depth relative to the surgical mesh and the second tissue anchor 402B is disposed at a deeper depth relative to the surgical mesh. In the embodiment shown in FIG. 13B, the slip knot 424 has passed through the mesh so that it is located between the posterior face of the anterior fascia and the peritoneum.

In one embodiment, as the first and second tissue anchors 402A, 402B are deployed into the tissue, the strand of surgical suture 408 pulls the tensioner 410 through the central channel 484 until the distal end of the tensioner 410 abuts against the proximal end of the stop 490.

Figure 13C:
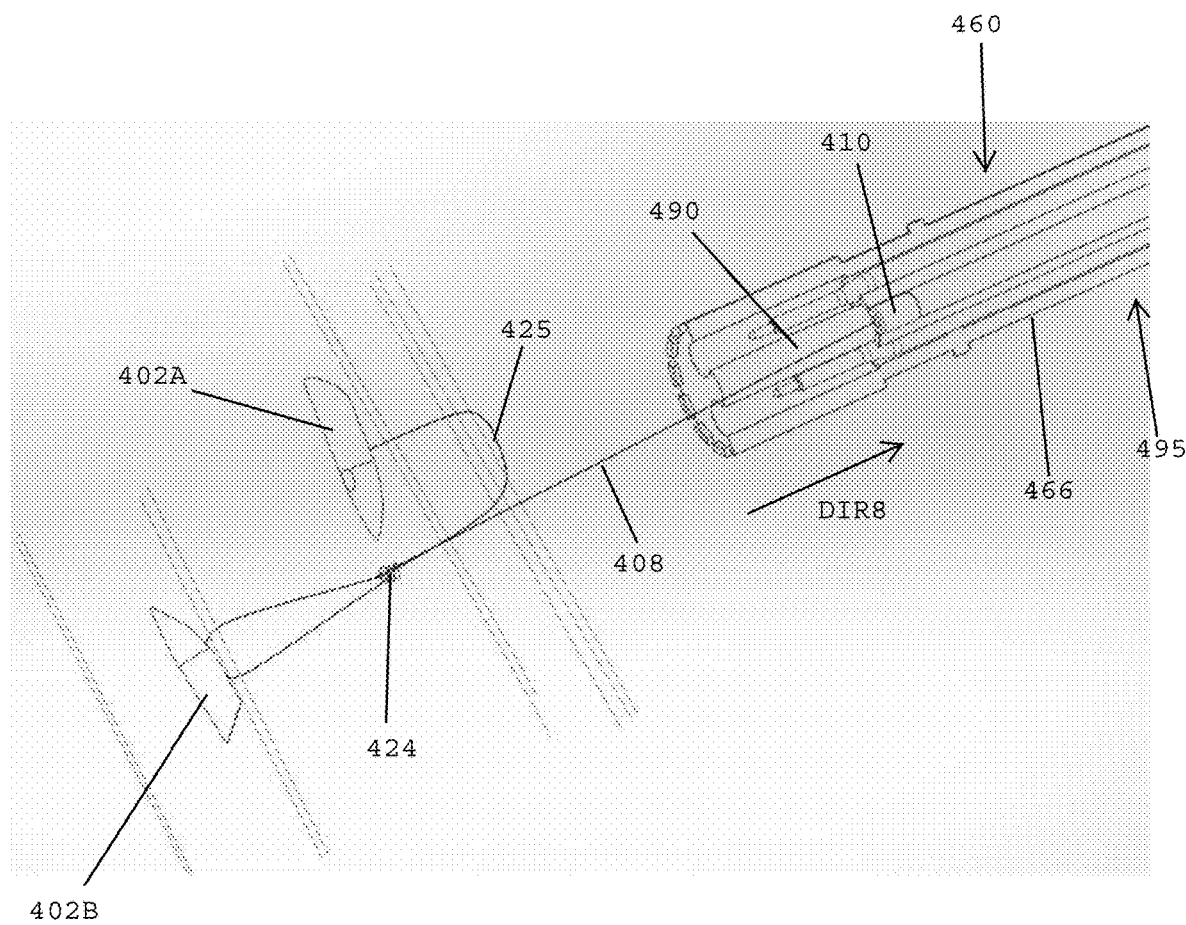

Referring to FIG. 13C, in one embodiment, after the first and second tissue anchors 402A, 402B have been implanted at the respective shallower and deeper depths, the insertion tool 495 may be retracted in the direction designated DIR8.

As the insertion tool 495 is retracted, the tensioner 410 abuts against the stop 490, which applies tension to the suture material 408 and moves the slip knot 424 closer to the second tissue anchor 402B. The orientation of the first and second tissue anchors 402A, 402B may toggle as tension is applied to the suture material. The single strand of suture material 425 extending between the first tissue anchor 402A and the slip knot 424 passes over the posterior face of the surgical mesh to act as a pledget described above in the embodiment shown in FIG. 1. When sufficient tension has been applied to the suture material 408 for reliably securing the surgical mesh over the peritoneum layer, a free end of the suture material 408 may be cut for uncoupling the cartridge 460 and the tensioner 410 from the implanted tissue anchors 402A, 402B.

Figure 14:
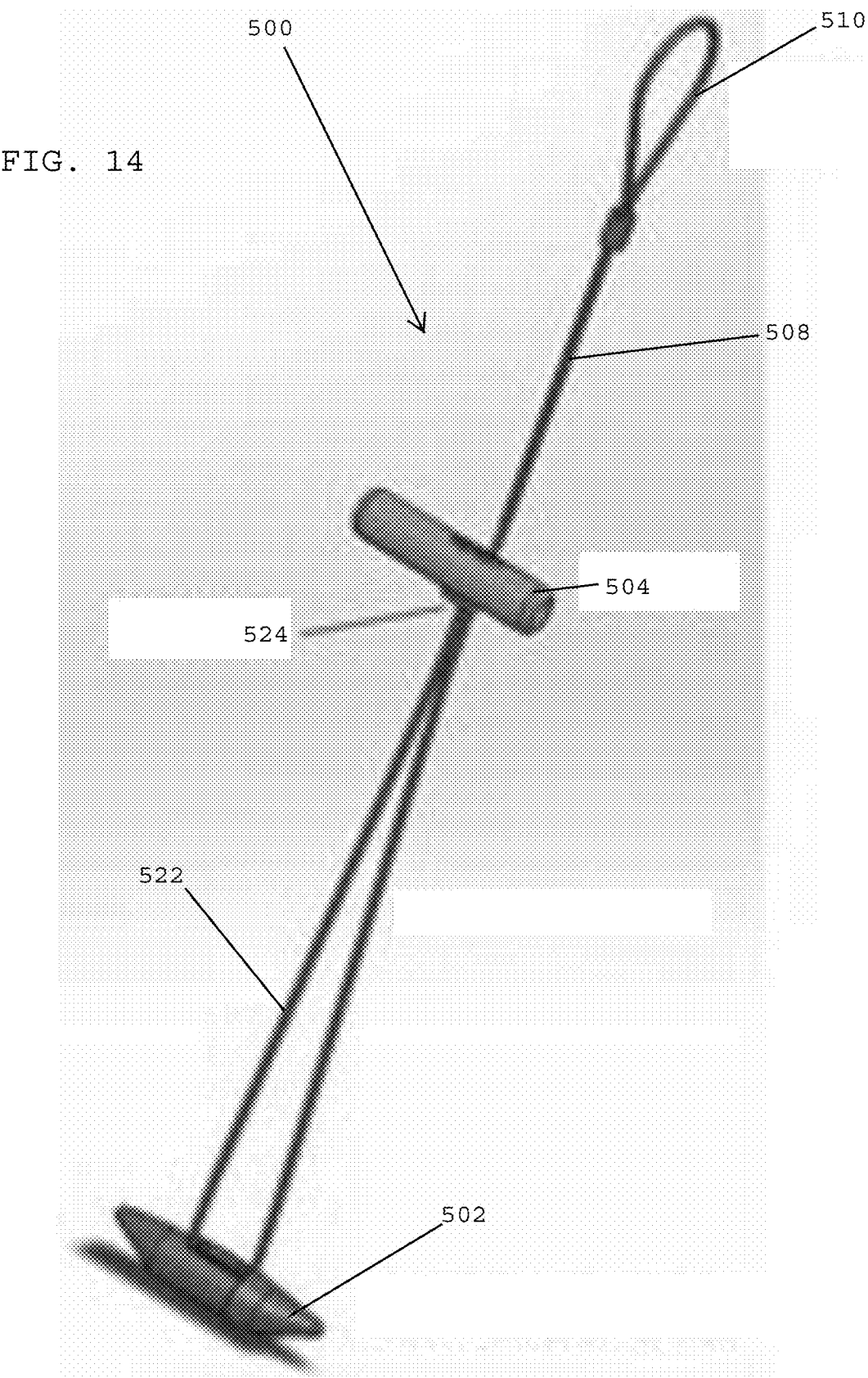
FIG. 14 shows a suture implant including a tissue anchor, a pledget, a pulling loop, and suture including a suture loop and a slip knot, in accordance with one embodiment of the present patent application.

Referring to FIG. 14, in one embodiment, a suture implant 500 desirably includes a tissue anchor 502, a pledget 504 and a suture 508 having a first end including a pulling loop 510. In one embodiment, the suture material 508 includes a suture loop 522 having a closed end that passes through the tissue anchor 502 and a slip knot 524 disposed between an underside of the pledget 504 and the tissue anchor 502. In one embodiment, as the pulling loop 510 is pulled away from the tissue anchor 502, the slip knot 524 and the pledget 504 move toward the tissue anchor 502 for applying a compressing force between the pledget and the tissue anchor.

Figure 15A:
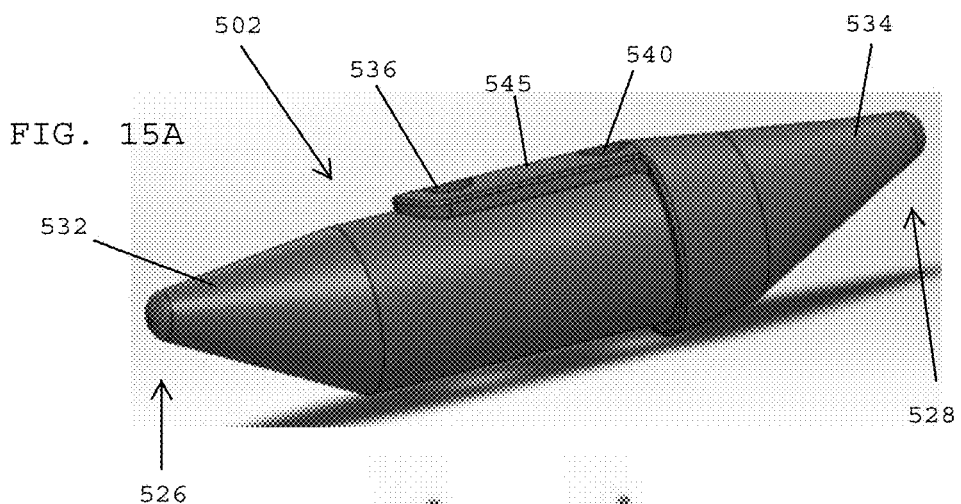
FIGS. 15A and 15B show the tissue anchor of FIG. 14, in accordance with embodiment of the present patent application.

Referring to FIG. 15A, in one embodiment, the tissue anchor 502 desirably includes a proximal end 526 and a distal end 528. The proximal end 526 has a first pointed tip 532 and the distal end 528 has a second pointed tip 528. The topside of the tissue anchor 502 desirably includes a pair of openings 536, 540 adapted to receive the suture loop 522 (FIG. 14). The tissue anchor is free to toggle relative to the suture loop so that the tissue anchor may be oriented along a first axis during deployment and a second axis after tension is applied to the suture implant.

In one embodiment, the tissue anchor 502 includes an attachment flange 545 that defines a slightly thicker area located in a midsection of the tissue anchor 502. The attachment flange 545 enables the tissue anchor 502 to be releasably secured to a distal end of a delivery device, as will be described in more detail below.

Figure 15B:
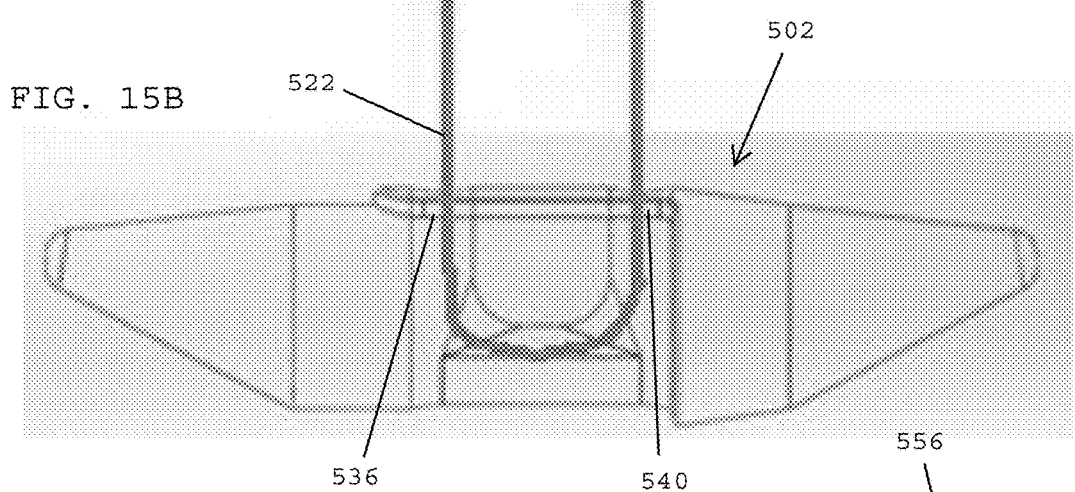

Referring to FIG. 15B, in one embodiment, a closed end of a suture loop has a first strand that passes through the first opening 536 and a second strand that passes through the second opening 540. The closed end of the suture loop 522 passes between the first and second openings 536, 540 and within the tissue anchor 502. The tissue anchor 502 is able to toggle relative to the closed end of the suture loop 522 for assuming different orientations relative to the suture loop 522.

Figure 16:
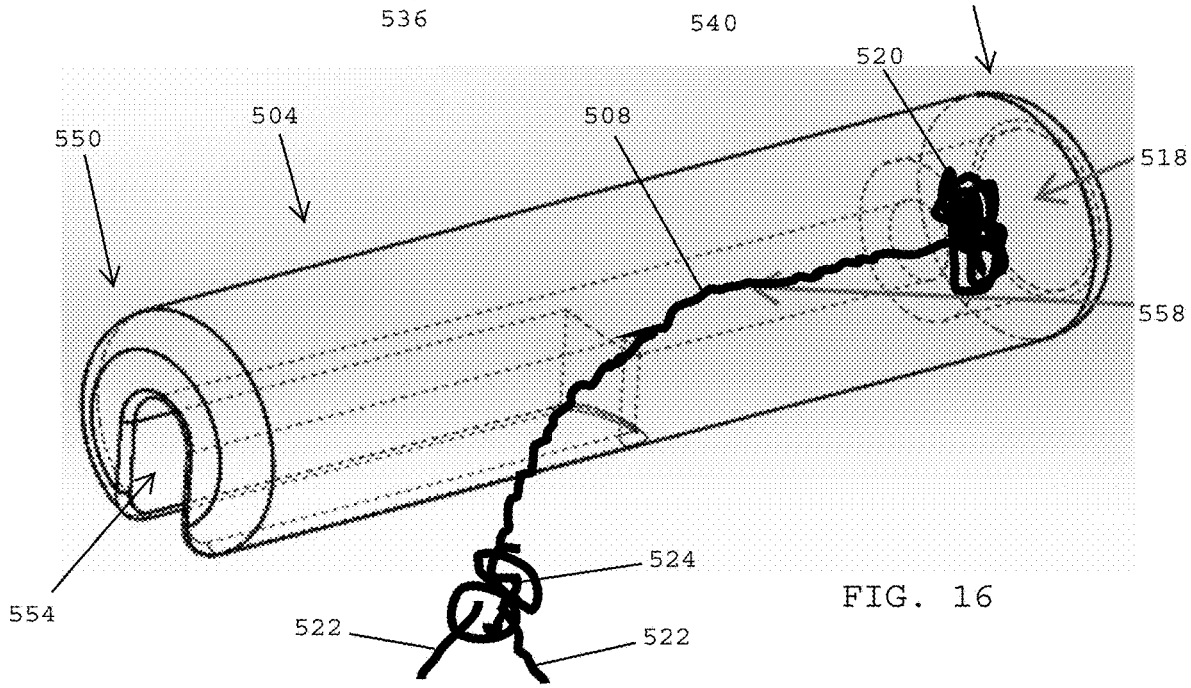
FIG. 16 shows the pledget of FIG. 14, in accordance with one embodiment of the present patent application.

Referring to FIG. 16, in one embodiment, the pledget 504 preferably has a first end 550 and a second 556. The pledget 504 preferably includes an elongated slot 554 that desirably extends from the first end 550 toward the second end 556. The pledget 504 desirably includes a recess 518 adapted to receive a knot formed at a free end of the suture material and an elongated conduit 558 that extends between the knot recess 518 and the elongated slot 554.

In one embodiment, the pledget 504 is coupled with the suture 508 by forming a knot 520 at a free end of the suture 508 whereby the knot 520 is disposed within the knot recess 518. The suture 508 is preferably passed through the elongated conduit 558 and through the elongated slot 554 with the slip knot 524 positioned below the pledget 504 and in general alignment with the opening of the elongated slot 554 along the underside of the pledget 504. In one embodiment, the suture loop 522 desirably extends from the slip knot 524.

Figure 17A:
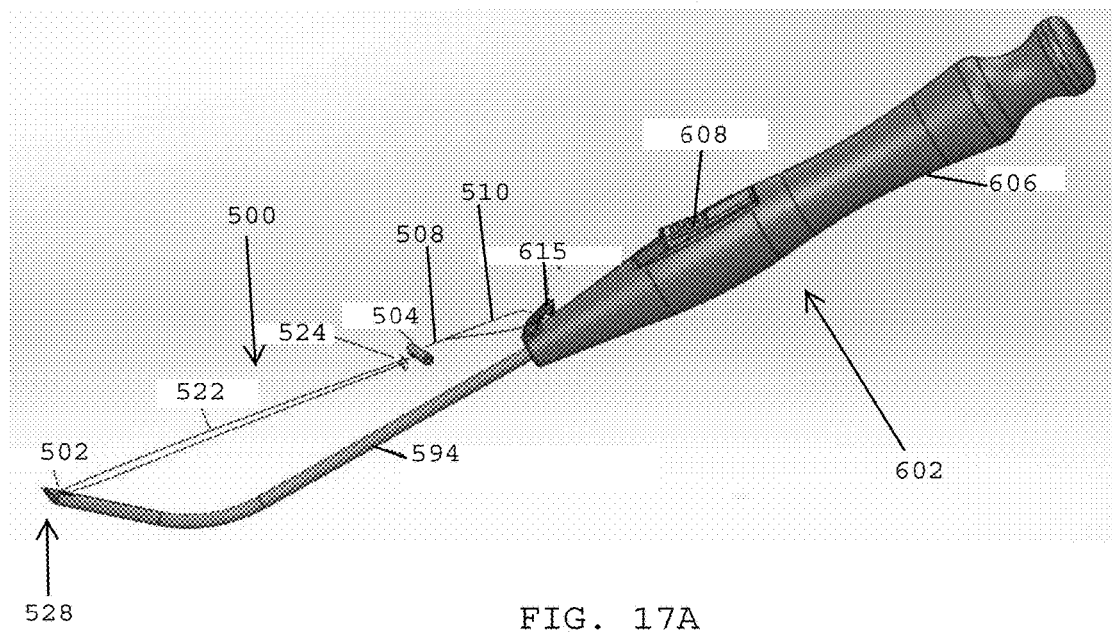
FIGS. 17A and 17B show a delivery device utilized for implanting the suture implant of FIG. 14, in accordance with one embodiment of the present patent application.
Figure 17B:
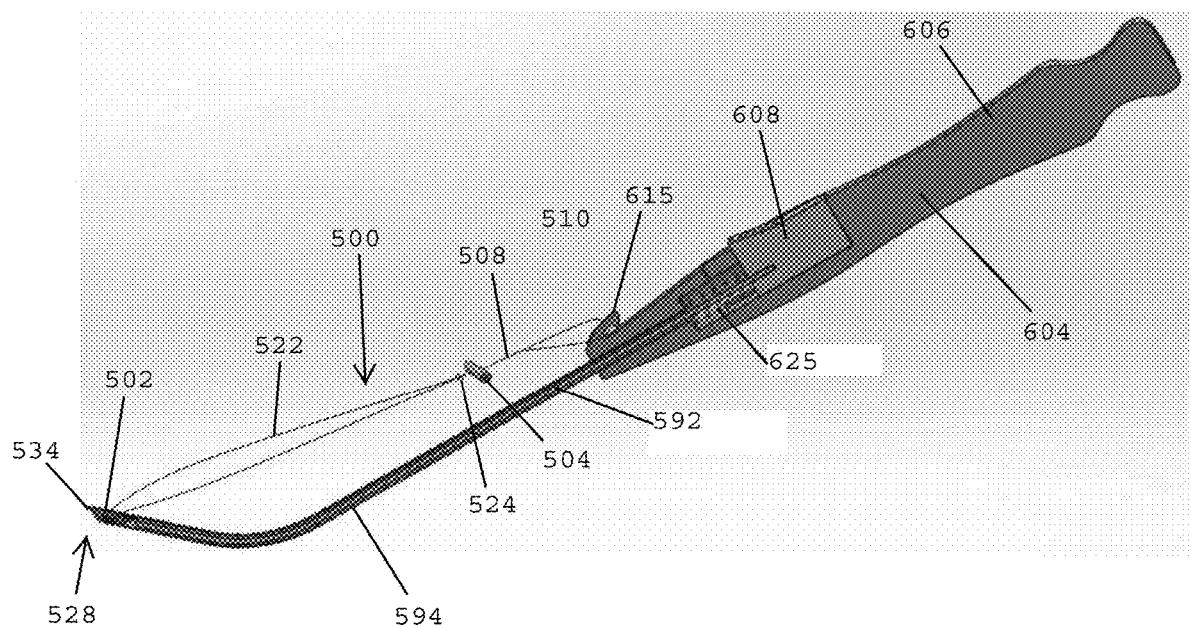

Referring to FIGS. 17A and 17B, in one embodiment, a delivery device 602 is utilized for implanting the suture implant 500 in tissue, and applying tension to the suture material 508. In one embodiment, the insertion tool 602 preferably includes a housing 604 having a handgrip 606, a tissue anchor release button 608 and a suture loop catcher 615. An elongated hollow shaft 594 extends from a distal end of the housing 604. A pushing shaft 592 is disposed within the hollow elongated shaft 594 for detaching and/or releasing the tissue anchor 502 from an attachment with the distal end of the elongated hollow shaft 594. In one embodiment, the insertion tool 602 desirably includes a return spring 625 disposed within the housing 604. The return spring 625 normally urges the release button 608 toward the proximal end of the handle 606. The return spring 625 is disposed within the housing 604 and extends between the release button 608 and a stop wall formed within the housing 604. In one embodiment, when the release button 608 is pushed toward the distal end of the elongated shaft 594, the pushing shaft 592 moves distally for pushing and/or detaching the tissue anchor 502 from the distal end of the elongated shaft 594 so as to release the tissue anchor 502 from an attachment with the insertion tool 602. When the release button 608 is no longer pushed distally, the return spring 625 utilizes the energy stored therein for returning the release button 608 to a proximal position. Energy is stored in the return spring 625 each time the release button 608 is pushed toward the distal end of the elongated shaft and, when the released button is released, the stored energy returns the release button 608 back to the proximal position shown in FIG. 17B.

In one embodiment, the suture implant 500 is loaded onto the insertion tool 602 by inserting the pointed tip 532 at the proximal end 526 (FIG. 15A) of the tissue anchor 502 into the opening at the distal-most end of the hollow elongated shaft 594. The distal end 528 with the pointed tip 534 preferably projects from the distal end of the hollow elongated shaft 594. The pulling loop 510 is desirably hooked around the suture loop catcher 615 with the suture material 508 including the suture loop 522 extending between the suture loop catcher 615 and the tissue anchor 502. The suture includes the slip knot 524 formed therein and the pledget 504 is disposed between the slip knot 524 and the suture pulling loop 510.

Figure 18A:
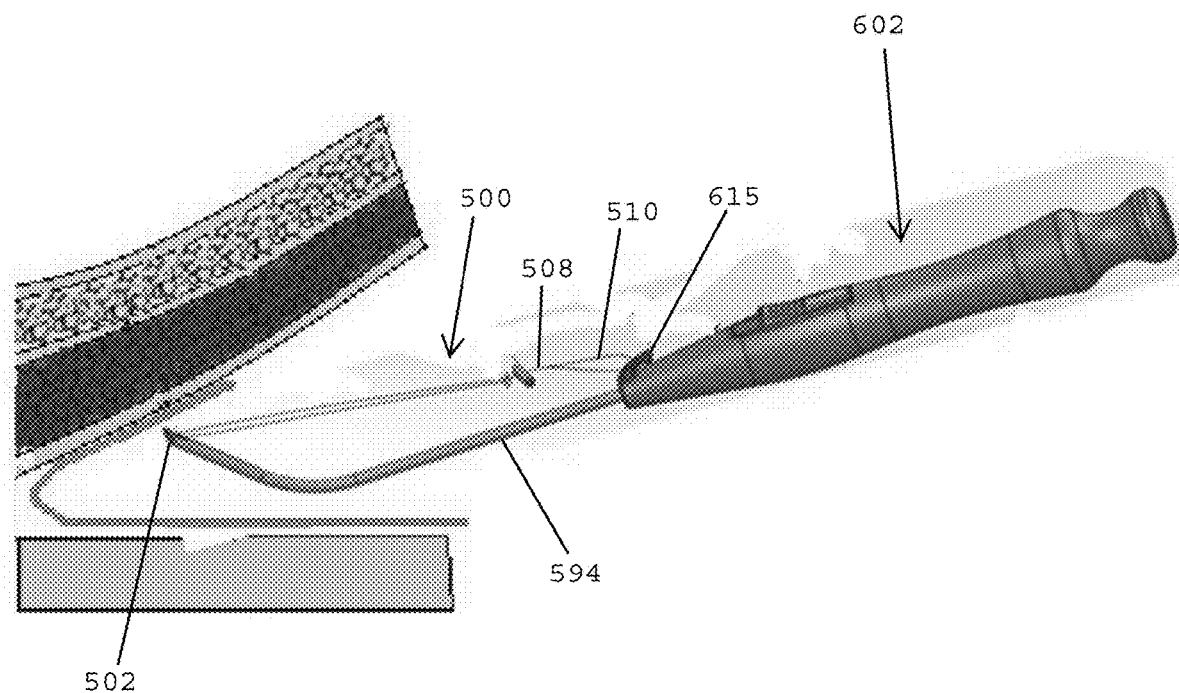
FIGS. 18A-18C show a method of utilizing the insertion tool of FIGS. 17A and 17B for implanting a suture implant, in accordance with one embodiment of the present patent application.

In one embodiment, the insertion tool 602 and the suture implant shown in FIGS. 14-17B is utilized for securing a surgical mesh to tissue during an open hernia repair procedure. Referring to FIG. 18A, in one embodiment, the suture implant 500 is loaded onto the insertion tool 602 so that the tissue anchor 502 is secured to the distal end of a hollow elongated shaft 594 and the pulling loop 510 of the suture material 508 is hooked onto the suture loop catcher 615 of the insertion tool 602. In one embodiment, a surgical mesh is unfurled over tissue having a hernia defect. The pointed tip 534 at the distal end 528 (FIG. 15A) of the tissue anchor 502 is juxtaposed with a major surface of the surgical mesh, which, in turn, overlies tissue of a patient.

Figure 18B:
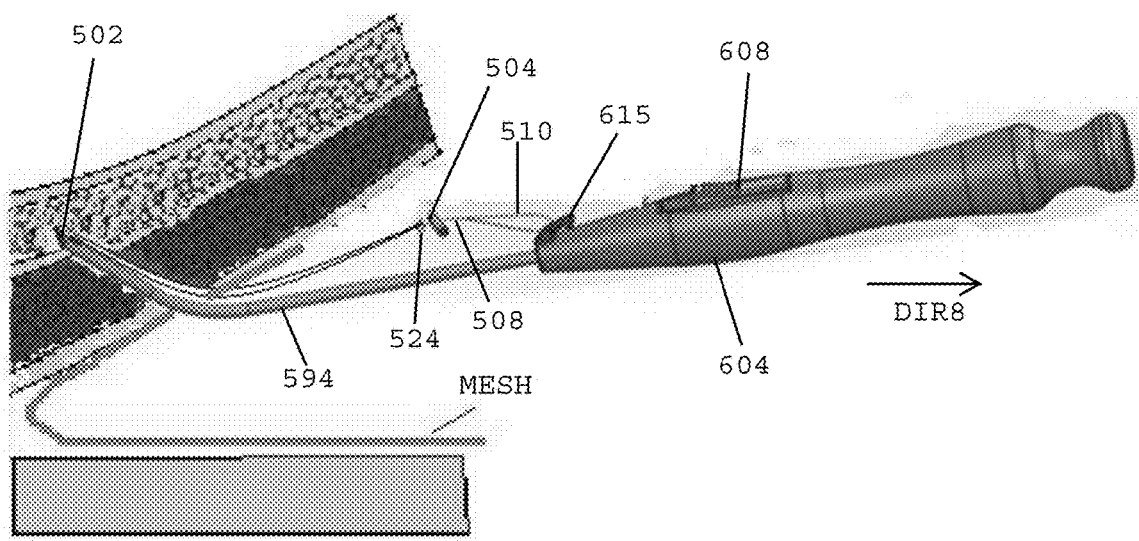

Referring to FIG. 18B, in one embodiment, the pointed tip of the tissue anchor 502 is advanced through the surgical mesh and the peritoneum layer until it is disposed within the anterior fascia layer of a patient. In one embodiment, the tissue anchor 502 preferably remains secured to the distal end of the elongated shaft 594 as the tissue anchor 502 is passed through the mesh, the peritoneum layer, and into the anterior fascia. Once the tissue anchor 502 is disposed within the anterior fascia layer, the release button 608 may be advanced toward the distal end of the housing 604 to advance the push off flexible shaft 594 (FIG. 17B) distally to detach and/or decouple the tissue anchor 502 from the distal end of the elongated shaft 594.

In one embodiment, once the tissue anchor 502 has been detached from the distal end of the elongated shaft 594, the insertion tool may be retracted in the direction designated DIRE, whereupon the suture loop catcher 615 pulls on the pulling loop 510 to apply tension to the suture material 508. As tension is applied to the suture material 508, the pledget 504 and the slip knot 524 advanced toward the posterior surface of the surgical mesh for applying compression to the surgical mesh overlying the peritoneum layer. When appropriate tension has been applied to the suture material, the free end of the suture material may be cut between the pledget 504 and the pulling loop 510.

Figure 18C:
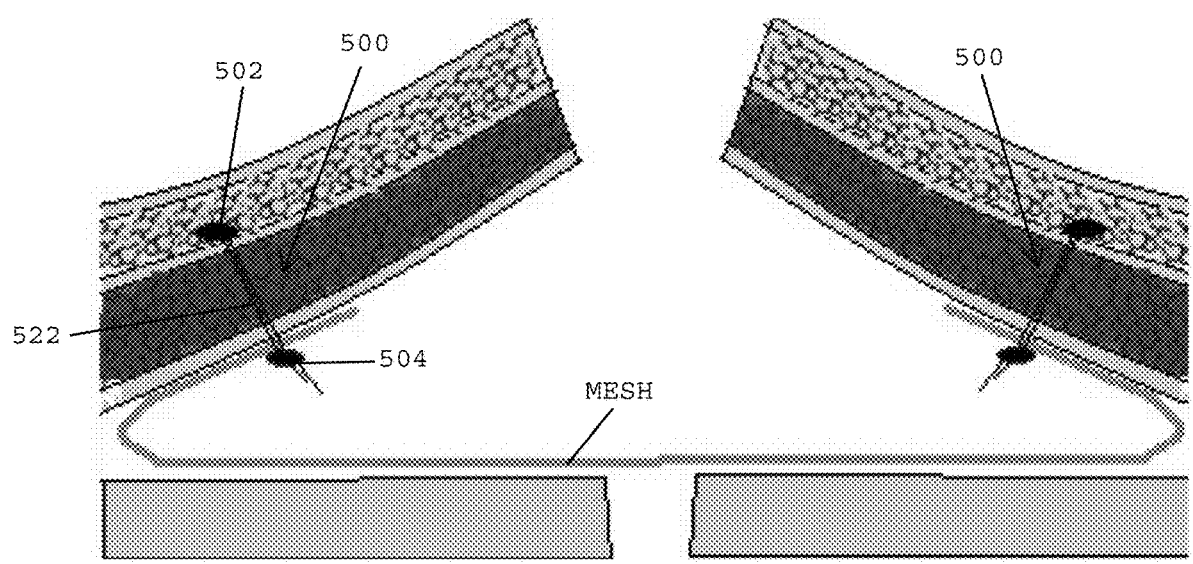

FIG. 18C shows suture implants securing a surgical mesh to tissue. Each suture implant 500 includes the tissue anchor 502 disposed within the anterior fascia layer, the suture loop 522 extending between the tissue anchor 502 and the pledget 504 whereby tension has been applied to the suture material so that the pledget 504 applies a compression force on a major surface of the surgical mesh for securing the surgical mesh in place relative to the underlying tissue. In one embodiment, multiple suture implants 500 may be utilized for securing the surgical mesh to tissue for repairing a hernia defect.

Figure 19A:
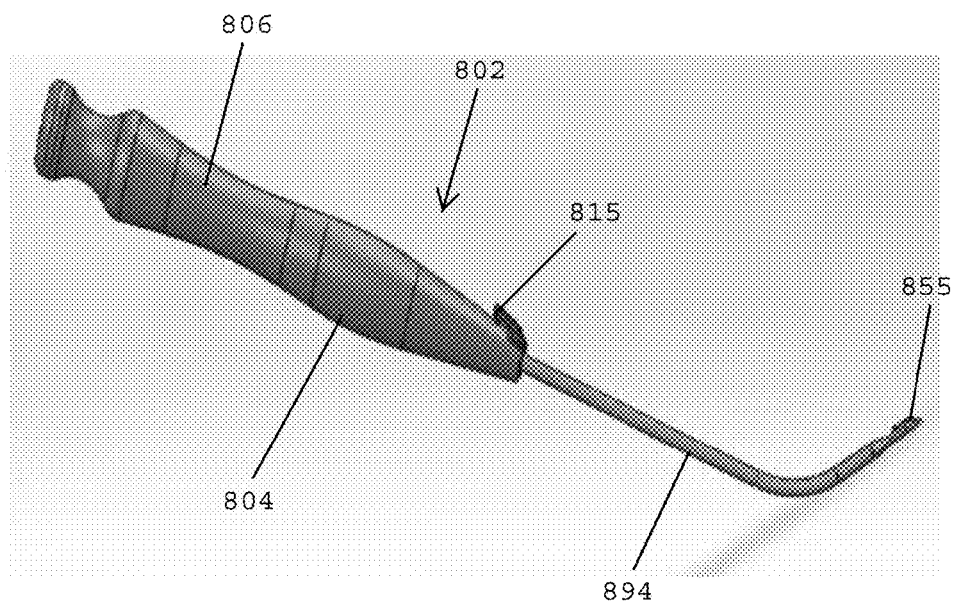
FIGS. 19A and 19B show a delivery device for inserting a suture implant into tissue, in accordance with one embodiment of the present patent application.
Figure 19B:
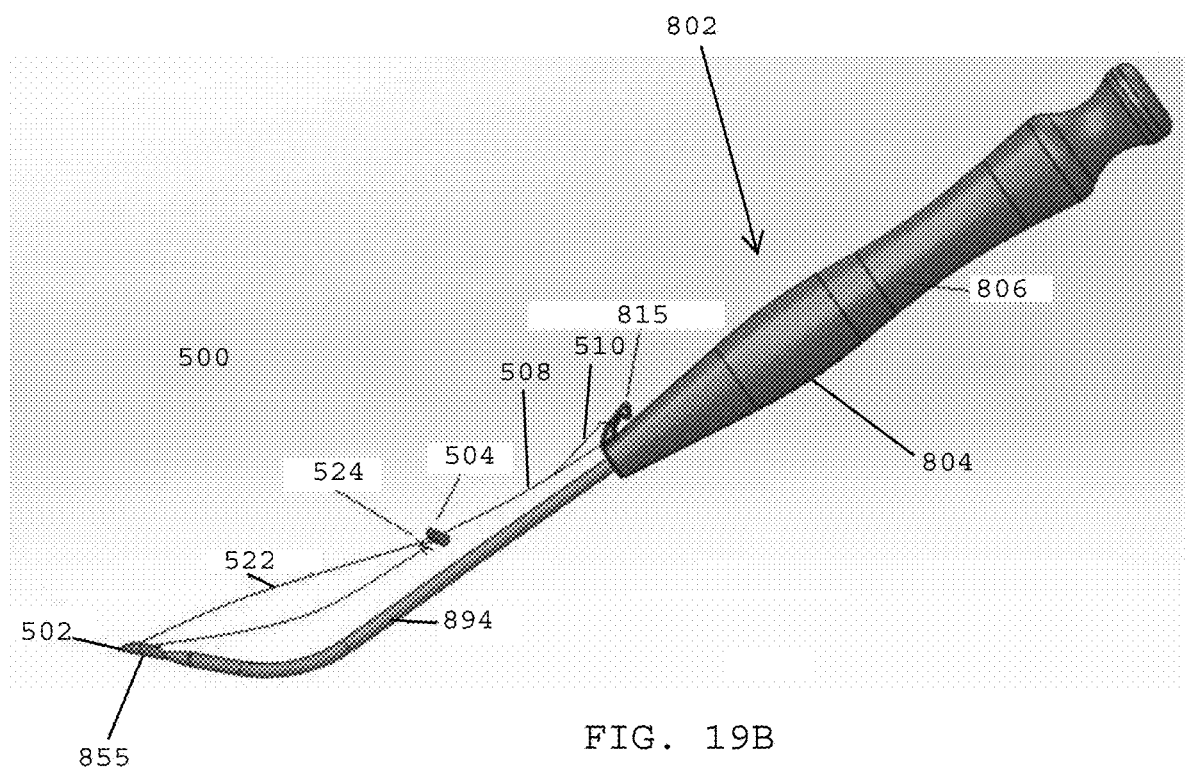

Referring to FIGS. 19A and 19B, in one embodiment, a delivery device 802 includes a housing 804 and a handgrip 806 extending proximally from the housing 804. The insertion tool 802 includes a suture loop catcher 815 and an elongated shaft 894 that extends from a distal end of the housing 804. The distal most end of the elongated shaft 894 has a cradle 855 adapted to form a friction fit engagement with a tissue anchor as shown and described above in FIG. 14. In one embodiment, the suture implant shown and described above in FIG. 14 may be assembled with the insertion tool 802. In one embodiment, the tissue anchor 802 engages the cradle 855 at the distal end of the elongated shaft 894 to form a friction fit between the anchor 802 and the elongated shaft 894. The suture material 508 preferably includes the pulling loop 510 which is hooked onto the suture loop catcher 815, a suture loop 522 that extends between the tissue anchor 802 and the slip knot 524, and a pledget 504 that is disposed between the slip knot 524 and the pulling loop 510.

Figure 20A:
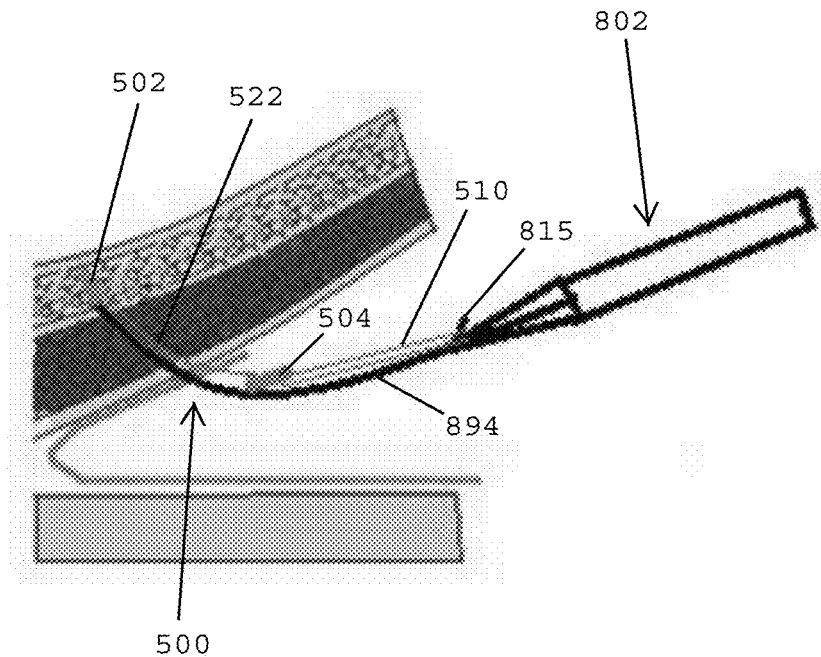
FIGS. 20A and 20B show a method of utilizing the insertion tool of FIGS. 19A and 19B for implanting a suture implant in tissue during an open hernia repair procedure, in accordance with one embodiment of the present patent application.
Figure 20B:
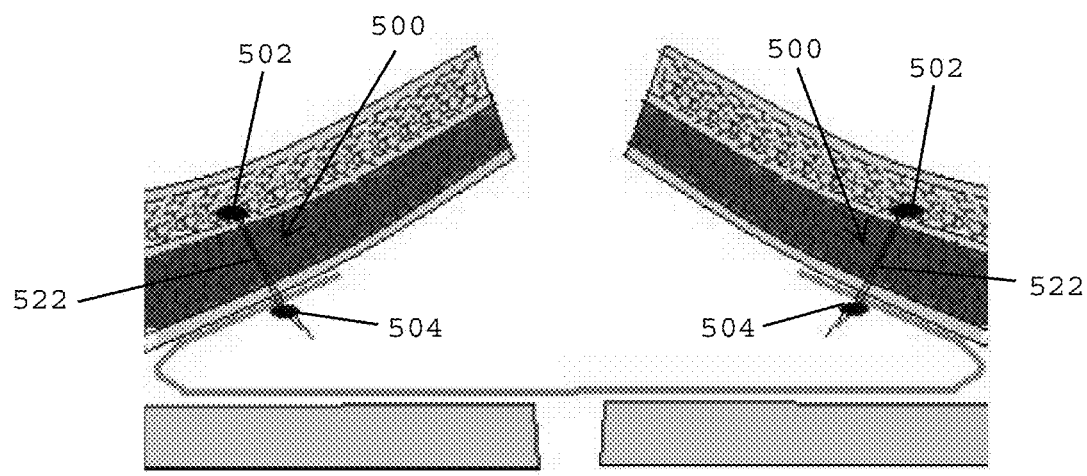

Referring to FIG. 20A, in one embodiment, after the suture implant 500 has been assembled with the insertion tool 802, the distal end of the elongated shaft 894 is advanced through a surgical mesh and into tissues so that the tissue anchor 802 is disposed within an anterior fascia layer. The insertion tool 802 may be retracted whereupon the interaction of the pulling loop 510 with the suture loop catcher 815 applies tension to the suture material so that that the slip knot 524 and the pledget 504 (FIG. 14) move toward the tissue anchor 502. After sufficient tension has been applied to the suture material, the free end of the suture material between the pledget 504 and the pulling loop 510 may be cut. FIG. 20B shows two suture implants 500 securing a surgical mesh to tissue. The tissue anchors 502 are disposed within the anterior fascia layer, the suture loops 522 extend between the tissue anchors 502 and the pledgets 504, whereby sufficient tension exists in the suture material between the tissue anchors 502 and the pledgets 504 for securing the surgical mesh in place over the underlying tissue.

Figure 21:
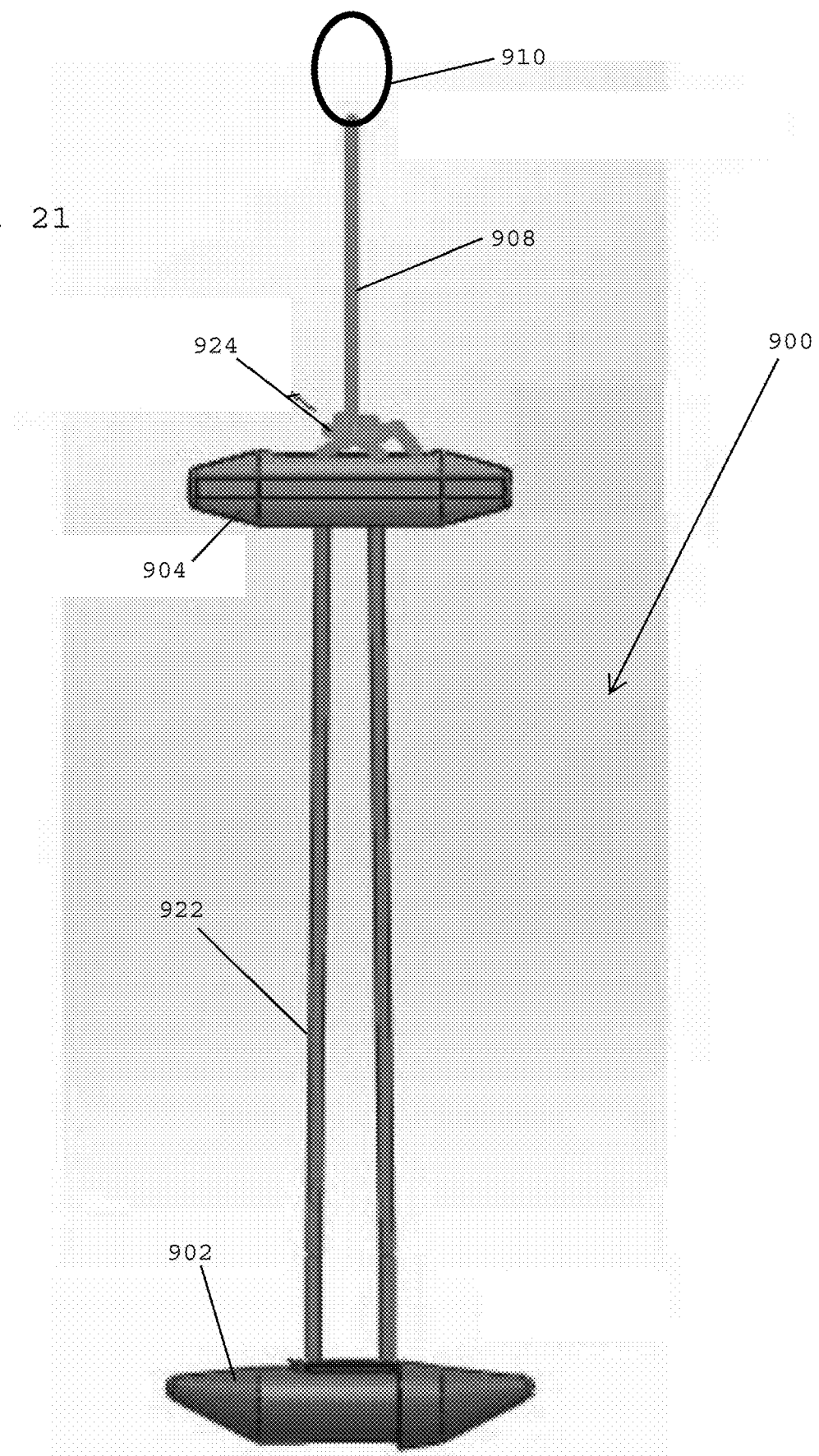
FIG. 21 shows a suture implant including a tissue anchor, a pledget, and suture material including a pulling loop, a suture loop, and a Roeder-type slip knot, in accordance with one embodiment of the present patent application.

Referring to FIG. 21, in one embodiment, a suture implant 900 may include a tissue anchor 902, a pledget 904, suture material 908 having a pulling loop 910 and a suture loop 922 extending between the pledget 904 and the tissue anchor 902. In one embodiment, the suture 908 includes a Roeder type slip knot 924 formed in the suture material. In one embodiment, the Roeder type slip knot 924 is preferably disposed between a top side of the pledget 904 and the pulling loop 910. In one embodiment, as the pulling loop 910 is pulled away from the tissue anchor 902, the Roeder type slip knot 924 and the pledget 904 move toward the tissue anchor 902 for applying a compressing force between the underside of the pledget 904 and the top side of the tissue anchor 902.

Figure 22:
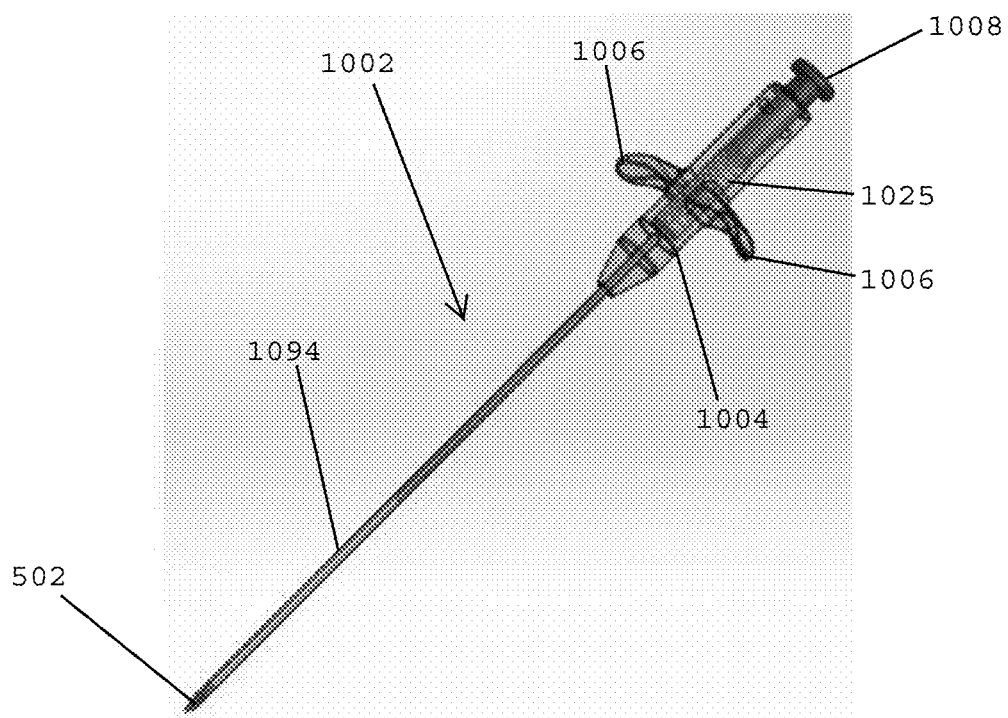
FIG. 22 shows a perspective view of a delivery device utilized for implanting a suture implant in tissue, in accordance with one embodiment of the present patent application.

Referring to FIG. 22, in one embodiment, a delivery device 1002 for a suture implant preferably includes a housing 1004 having a finger grip 1006 and a release plunger 1008 disposed at a proximal end of the housing 1004. The insertion tool 1002 desirably includes a return spring 1025 having a distal end abutting against a stop wall within the housing 1002 and a proximal end in contact with the release plunger 1008. The insertion tool 1002 desirably includes a hollow elongated shaft 1094 including a driver rod that has a proximal end coupled with the release plunger 1008.

In one embodiment, a suture implant including a tissue anchor 502 (FIG. 14) is inserted into a distal end of the elongated hollow shaft 1094. In one embodiment, the release plunger 1008 is pushed toward the distal end of the elongated shaft 1094 whereupon the pusher rod pushes the tissue anchor 502 off of the attachment with the distal end of the elongated shaft 1094. When the release plunger 1008 is pushed toward the distal end of the elongated shaft 1094, energy is stored in the return spring 1025. When distally directed force is removed from the release plunger 1008, the energy stored in the return spring 1025 returns the release plunger 1008 to the extended position shown in FIG. 22

Figure 23A:
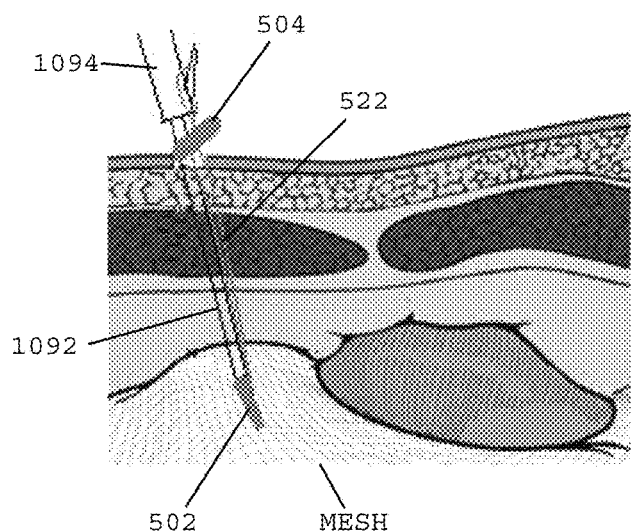
FIGS. 23A-23D show a method of utilizing the insertion tool of FIG. 22 for implanting a suture implant in tissue during a closed hernia repair procedure, in accordance with one embodiment of the present patent application.

The insertion tool 1002 shown in FIG. 22 may be utilized during a hernia repair procedure. Referring to FIG. 23A, in one embodiment, a distal end of the elongated shaft 1094 is juxtaposed with a skin surface. A cut may be made in the skin surface. In one embodiment, the plunger 1008 (FIG. 22) is preferably moved toward the distal end of the elongated shaft 1094 for extending the pusher rod 1092 from the distal end of the elongated shaft 1094. The pusher rod 1092 advances the tissue anchor 502 through the skin opening, the anterior fascia layer and the peritoneum, and the surgical mesh so that the tissue anchor 502 has passed through the surgical mesh as shown in FIG. 23A.

Figure 23B:
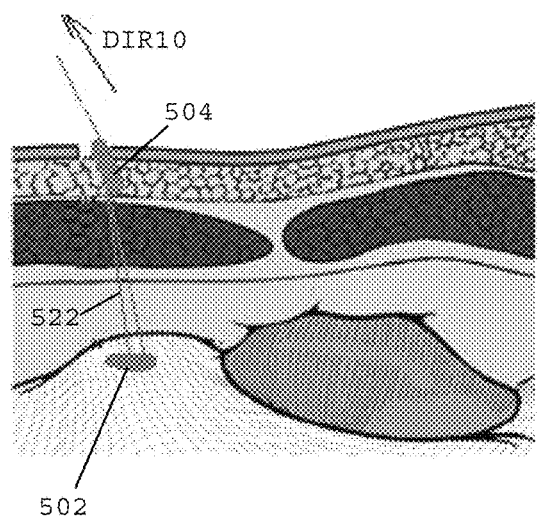

Referring to FIG. 23B, in one embodiment, the tissue anchor 502 may toggle relative to the closed end of the suture loop 522 for assuming the configuration shown in FIG. 23B. The insertion tool including the elongated shaft 1094 may be retracted from the skin opening in a direction designated DIR10 to apply tension to the suture material. As tension is applied to the suture material, the slip knot and the pledget 504 are dispensed from the distal end of the elongated shaft and the pledget may be slid into the cut in the skin.

Figure 23C:
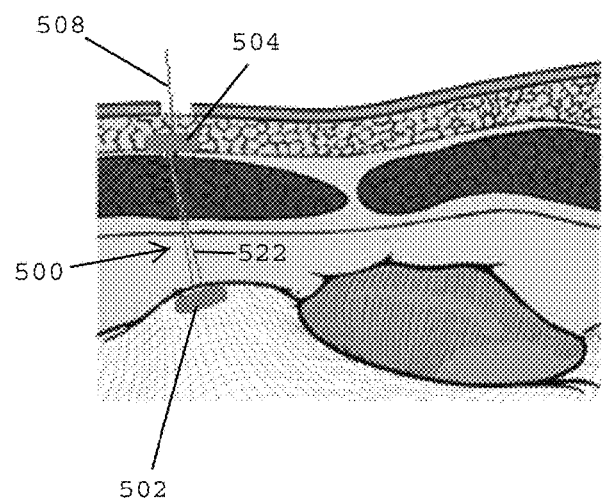
Figure 23D:
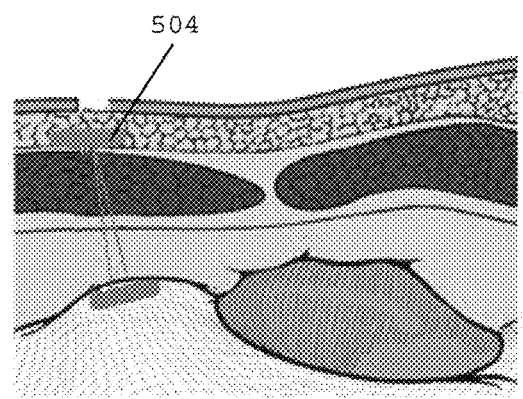

Referring to FIG. 23, the tissue anchor 502 and the pledget 504 may be toggled into the orientations shown in FIG. 23C for pulling the surgical mesh against the tissue and applying a compression force between the tissue anchor 502 and the pledget 504. At this stage, the tail of the suture material 508 extends out of the cut in the skin. Referring to FIG. 23D, in one embodiment, the free end or tail of the suture material may be cut above the pledget 504 for detaching the suture implant 500 from the insertion tool.

Figure 24:
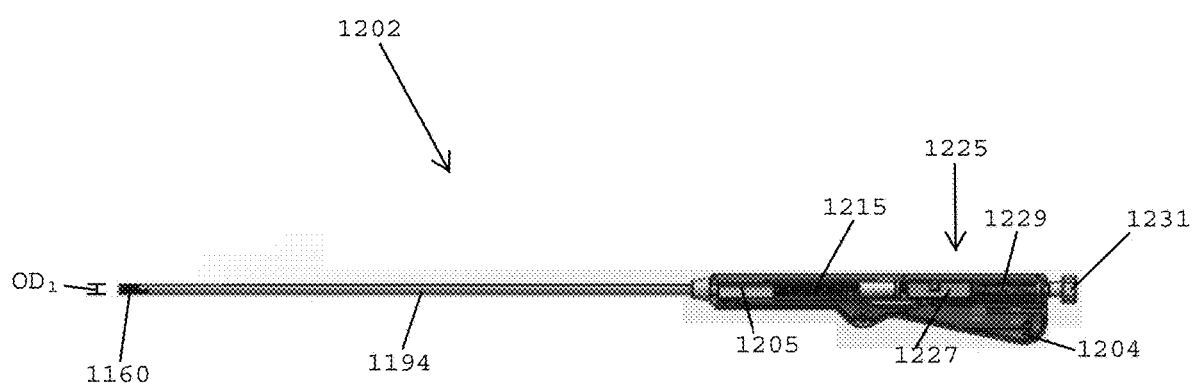
FIG. 24 shows a delivery device for dispensing a suture implant, the delivery device having a handle, a retractable cannula, and a reloadable cartridge containing a suture implant, in accordance with one embodiment of the present patent application.

Referring to FIG. 24, in one embodiment, a system for deploying a suture implant preferably includes a delivery device 1202 having a handle 1204, a retractable cannula 1194, and a reloadable cartridge 1160 that contains a suture implant (e.g., suture implant 100 shown in FIG. 1). In one embodiment, the cannula 1194 desirably has an outer diameter $OD_1$ of about 5 mm. In one embodiment, the delivery device 1202 desirably includes a cannula sled 1205 connected with a proximal end of the cannula 1194, and a cannula return spring 1215 disposed inside the handle 1204 of the delivery device 1202 that engages the cannula sled 1205 for normally urging the cannula 1194 into an extended position.

In one embodiment, the delivery device 1202 has a stored energy system 1225 for dispensing a suture implant from the reloadable cartridge 1160. In one embodiment, the stored energy system 1225 includes a driver sled 1227, a stored energy spring 1229, and a retractable button 1231 for storing energy in the stored energy spring 1229. In one embodiment, energy is stored in the stored energy spring 1229 by pulling the retractable button 1231 in a proximal direction (e.g., away from the reloadable cartridge 1160). In one embodiment, the stored energy system 1225 provides energy for driving the tissue anchor (e.g., tissue anchor 102 shown in FIG. 1) through a deployed surgical mesh and into tissue. In one embodiment, the stored energy is used to penetrate a relatively tough surgical mesh layer so that the tissue anchor may be advanced through the mesh layer. In one embodiment, the released of the energy stored in the stored energy system 1225 is triggered by the retractable cannula 1194 when the distal end of the cannula is pressed against an opposing surface (e.g., a mesh surface or a tissue surface).

In one embodiment, once the tissue anchor of the suture implant penetrates the mesh layer, an operator may continue to push the handle 1204 in a distal direction for allowing a surgeon to control the depth of penetration of the tissue anchor into tissue. In one embodiment, the surgeon may advance the tissue anchor so that it penetrates the underlying tissue layers and reaches the skin layer. In one embodiment, once the desired penetration depth has been achieved, the surgeon may retract the delivery device to drop the tissue anchor at the desired tissue layer. In one embodiment, the desired tissue layer is the anterior fascia layer. In one embodiment, when the delivery device is retracted, the dispensed tissue anchor toggles as the suture is being cinched so that the tissue anchor locks up on the fascia layer.

In one embodiment, the delivery device 1202 has a no-trigger design whereby only push and pull action is required for dispensing the suture implants from the cartridge 1160. In one embodiment, cinching of the suture occurs as the delivery device 1202 is pulled back from the mesh and the underlying tissue. In one embodiment, a system preferably includes a one or more reloadable cartridges, whereby each reloadable cartridge contains at least one suture implant (e.g., suture implant 100 shown in FIG. 1).

In one embodiment, a cutting blade may be attached to the cartridge 1160 for cutting the suture after the suture implant has been inserted into tissue and cinched.

Figure 25:
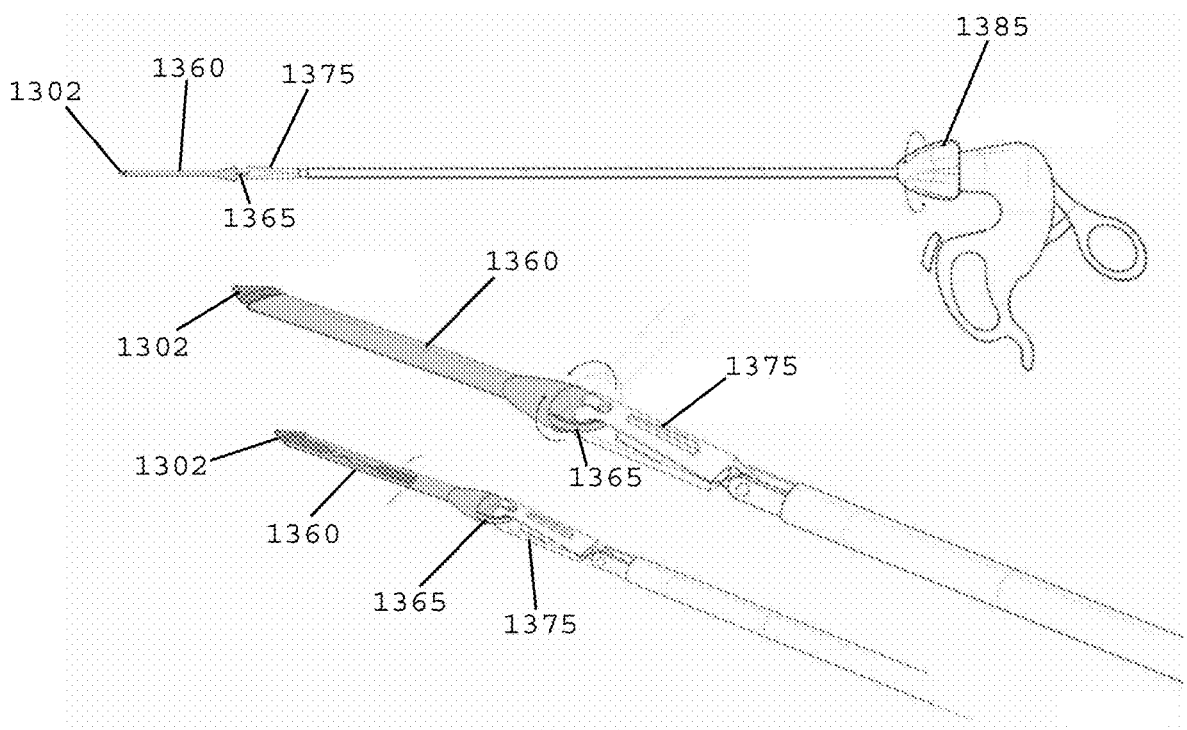
FIG. 25 shows a delivery device for dispensing a suture implant, in accordance with one embodiment of the present patent application.

Referring to FIG. 25, in one embodiment, a gripping flange 1365 on the proximal end of a reloadable cartridge 1360 allows the cartridge to be positioned and maneuvered by Laparoscopic graspers 1375. In one embodiment, use of small cartridges in conjunction with a standard grasper 1375 may reduce device size and cost. In one embodiment, the reloadable cartridge 1360 containing a transfascial suture implant has a self-stripping tissue anchor 1302.

Figure 26:
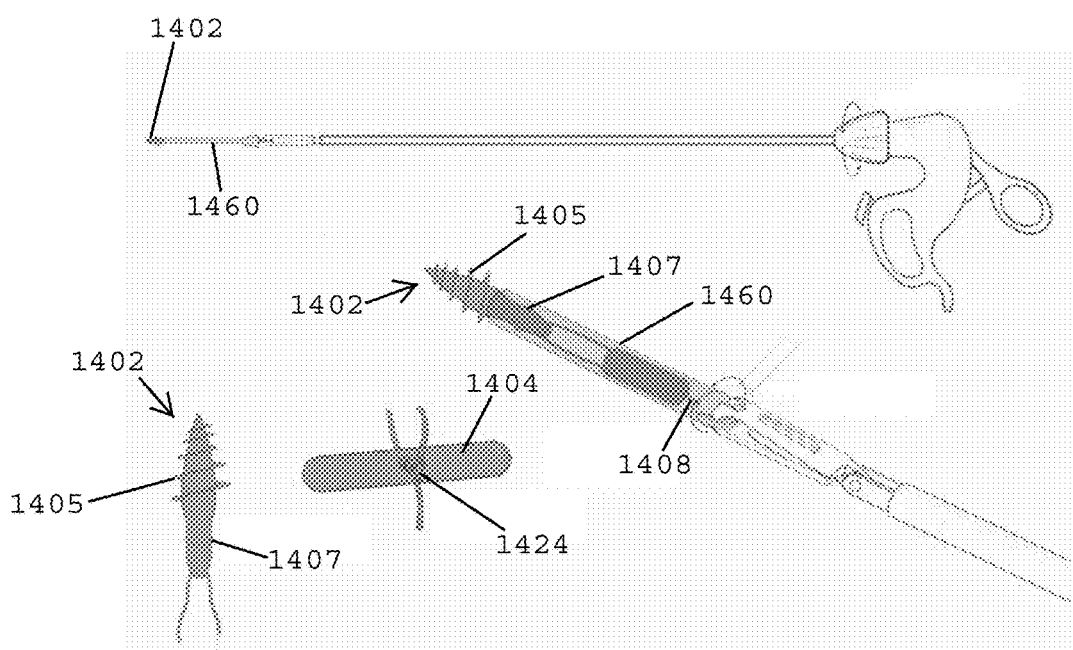
FIG. 26 shows a delivery device for dispensing a suture implant having a threaded tissue anchor, in accordance with one embodiment of the present patent application.

Referring to FIG. 26, in one embodiment, a tissue anchor 1402 may have threads 1405 to provide for a screw type tissue anchor. In one embodiment, providing threads on a screw type tissue anchor may increase holding force. In one embodiment, the suture implant includes a suture 1408 that is attached to the cartridge 1460 for cinching the suture implant. In one embodiment, the tissue anchor 1402 has a retention flange 1407 that releasably secures the tissue anchor 1402 within the cartridge 1460. In one embodiment, a suture includes a slip knot 1424 located inside a pledget 1404 for protecting the slip knot and minimizing patient irritation and/or pain.

Figure 27:
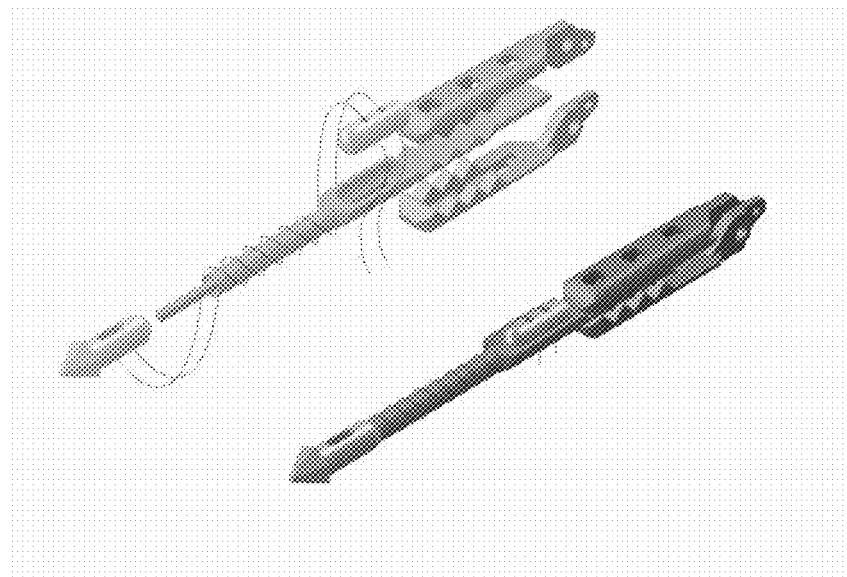
FIG. 27 shows a delivery device for dispensing a suture implant having a suture wrapped around a central shaft of the delivery device, in accordance with one embodiment of the present patent application.

Referring to FIG. 27, in one embodiment, a suture implant may include a suture wrapped around a central shaft of a delivery device and a pledget may be held in a pocket of the delivery device.

Figure 28:
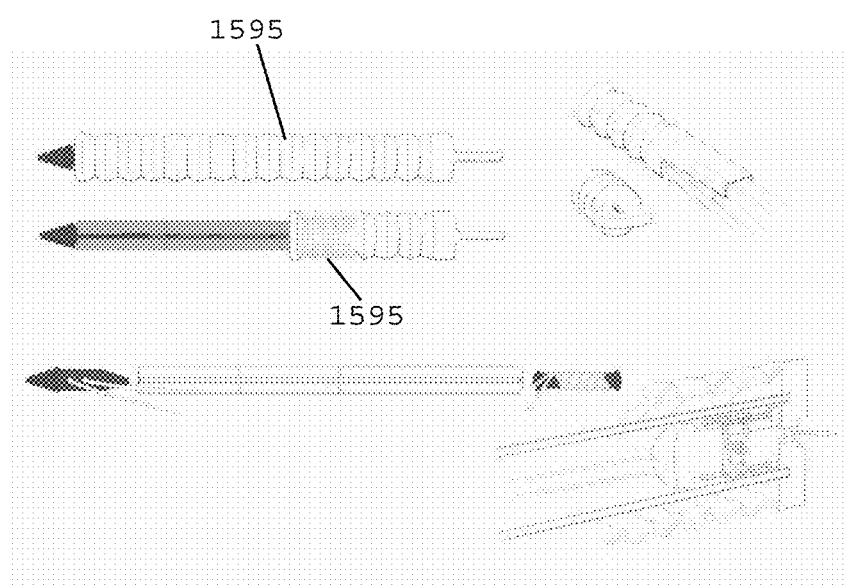
FIG. 28 shows a delivery device for dispensing a suture implant having a collapsible outer sheath, in accordance with one embodiment of the present patent application.

Referring to FIG. 28, in one embodiment, a delivery device may have a collapsible outer sheath 1595. The collapsible outer sheath 1595 may help to retain a self-stripping tissue anchor, manage a suture, and/or help a user to gauge the insertion depth of a tissue anchor.

Figure 29:
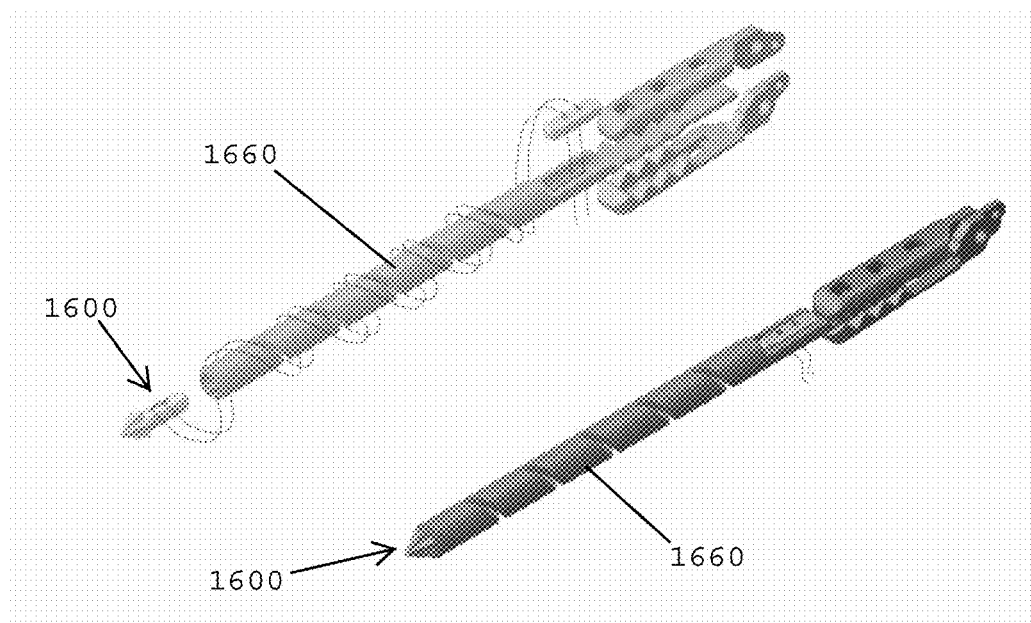
FIG. 29 shows a delivery device for dispensing a suture implant having an interrupted cartridge body, in accordance with one embodiment of the present patent application.

Referring to FIG. 29, in one embodiment, a cartridge that contains a suture implant may have an interrupted cartridge body 1660. In one embodiment, the interruptions in the cartridge body 1660 may help with assembly of the suture implant 1600 onto the cartridge.

Figure 30:
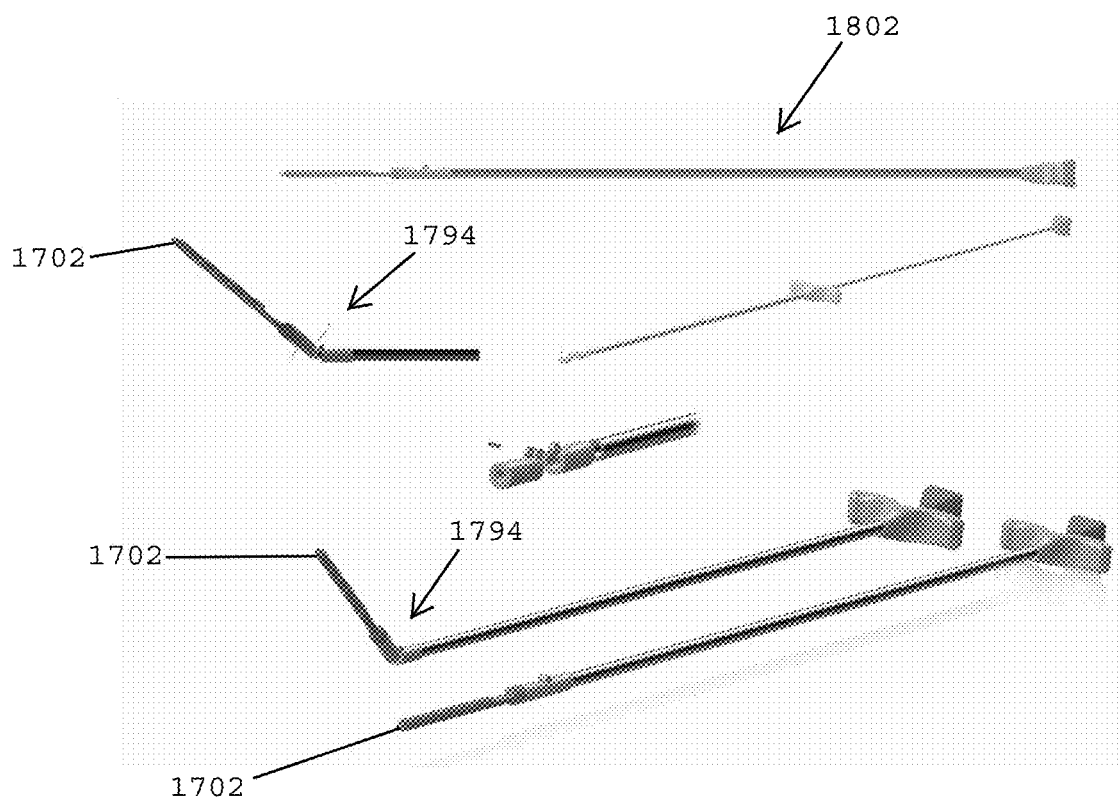
FIG. 30 shows a delivery device for dispensing a suture implant having an articulating shaft, in accordance with one embodiment of the present patent application.

Referring to FIG. 30, in one embodiment, a delivery device 1802 has an articulating shaft 1794, which may help a user to deliver a tissue anchor 1702 along an axis that is perpendicular to the tissue.

In one embodiment, the systems, devices and methods disclosed herein may be used during robotic surgical procedures such as hernia repair procedures. In one embodiment, the patient is prepared for surgery in administering anesthesia. In one embodiment, abdominal access may be prepared by inserting two or more ports through the abdominal wall and insufflating the abdominal cavity. In one embodiment, a surgical robot is attached to the pre-placed ports. The hernia site may be assessed under direct visualization using a laparoscopic camera. Adhesions are reduced and the peritoneum sac is excised if appropriate. A mesh is placed into the abdominal cavity. The surgeon selects from a variety of suture implants to identify one appropriate for the type of hernia repair being performed. The variety may include different tissue anchors, total number of tissue anchors on a suture implant, different suture loop lengths, different suture lengths, etc. In one embodiment, the cartridge is attached to the distal end of the delivery device. The distal end of an elongated shaft is advanced through one of the port openings. The housing or actuator end of the delivery device is attached to the arm of a surgical robot. During a surgical procedure, the distal end of the elongated shaft may be articulated if necessary to access areas requiring fixation, such as the ipsilateral side of the mesh, nearest the port. The delivery device may be used to dispense suture implants for securing surgical mesh to tissue. Cartridges can be changed for reloading or changing the type of suture implant being dispensed by the delivery device. In one embodiment, an articulated distal end is straightened before removing the device through the port.

In one embodiment, the systems and delivery devices disclosed herein may be coupled with and/or be in communication with a robotic surgical system, such as the systems and devices disclosed in US 2014/0005662 to Shelton, the disclosure of which is hereby incorporated by reference herein. In one embodiment, the robotic surgical system may have a sterile barrier located between the applicator instruments and surgical tools and the robotic part of the robotic surgical system, whereby the systems, delivery devices, cartridges and suture implants are located in the sterile environment.

In one embodiment, a robotic surgical system may have a master controller and control systems such as the systems and devices disclosed in U.S. Pat. No. 7,524,320, the disclosure of which is hereby incorporated by reference herein. The master controller may have control elements (e.g., knobs, actuators) that are engaged by a surgeon and manipulated in space while the surgeon views a surgical site through a video monitor and/or stereo display. The master controller may include manual input devices that move with multiple degrees of freedom. In one embodiment, the master control has an actuator for actuating surgical tools (e.g., dispensing a suture implant).

In one embodiment, the robotic surgical system may include a robotic cart that is configured to actuate a plurality of surgical tools and/or instruments. Various robotic surgery systems and methods employing master controller and robotic cart arrangements are disclosed in U.S. Pat. No. 6,132,368, the disclosure of which is hereby incorporated by reference herein. In one embodiment, a robotic cart may include a base from which surgical tools are supported. In one embodiment, the surgical tools may be supported by a series of manually articulatable linkages, generally referred to as set-up joints, and a robotic manipulator. These structures may have protective covers extending over much of the robotic linkage. The protective covers may be optional, and may be limited in size or entirely eliminated to minimize the inertia that is encountered by servomotors used to manipulate such devices, to limit the volume of moving components so as to avoid collisions, and to limit the overall weight of the robotic cart. In one embodiment, the robotic cart may have dimensions suitable for transporting the cart between operating rooms. The robotic cart is preferably configured to pass through standard operating room doors and onto standard hospital elevators. The robotic cart preferably has a weight and includes one or more wheels that allow the cart to be easily moved and positioned adjacent an operating table.

Other embodiments may incorporate a wide variety of alternative robotic structures, including those described in U.S. Pat. No. 5,878,193, the disclosure of which is hereby incorporated by reference herein. Additionally, while the data communication between a robotic component and the processor of the robotic surgical system is described with reference to communication between the surgical tool and the master controller, similar communication may take place between circuitry of a manipulator, a set-up joint, an endoscope or other image capture device, or the like, and the processor of the robotic surgical system for component compatibility verification, component-type identification, component calibration communication, and confirmation of coupling of the component to the robotic surgical system.

In one embodiment, during a surgical procedure, a surgeon may input control commands to the master controller or a control unit of the robotic surgical system, which "robotically-generates" output motions that are ultimately transferred to the systems and delivery devices disclosed herein. As used herein, the terms "robotically-generates" or "robotically-generated" refer to motions that are created by powering and controlling the motors of the robotic surgical system and other power driven components. These terms are distinguishable from the terms "manually-actuatable" or "manually generated" which refer to actions taken by a surgeon that result in control motions that are generated independent from those motions that are generated by powering the motors of the robotic surgical system.

While the foregoing is directed to certain embodiments of the present patent application, other and further embodiments may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the disclosed and claimed invention.

What is claimed is:

1. A system for deploying a suture implant comprising:
    a delivery device having an elongated shaft with a distal end;
    a suture implant coupled with said distal end of said elongated shaft, said suture implant including
        a suture having a first end, a second end, and a slip knot located between said first and second ends that defines a suture loop having a length, wherein said slip knot defines a dynamic end of said suture loop that is located opposite a closed end of said suture loop,
        a tissue anchor having first and second openings that are spaced from one another, wherein said closed end of said suture loop passes through said first and second spaced openings for securing said tissue anchor to said suture loop,
        a tensioner secured to said first end of said suture,
        a pledget secured to said second end of said suture and located between said tensioner and said tissue anchor, said pledget including a recess disposed inside said pledget that is located at a proximal end of said pledget, wherein said second end of said suture comprises a knot disposed in said recess of said pledget, and
        said slip knot being located between said tensioner and said tissue anchor, wherein pulling said tensioner away from said tissue anchor slides said pledget and said slip knot toward said tissue anchor for shortening the length of said suture loop and reducing the distance between said pledget and said tissue anchor.

2. The system as claimed in claim 1, wherein said tissue anchor comprises a proximal end with an angled face and a distal end with a tissue piercing point.

3. The system as claimed in claim 2, wherein said tissue anchor further comprises a mid-section located between said proximal and distal ends thereof that defines a closed outer surface at a top side of said tissue anchor that is bounded by said first and second openings.

4. The system as claimed in claim 3, wherein said tissue anchor further comprises:
    an elongated conduit that extends from said proximal end to said distal end of said tissue anchor;
    said first opening including a proximal elongated slot that is open at said top side of said tissue anchor and that extends from said angled face to said mid-section of said tissue anchor;
    said second opening including a distal elongated slot that is open at said top side of said tissue anchor and that extends from said tissue piercing point to said mid-section of said tissue anchor.

5. The system as claimed in claim 4, wherein said closed end of said suture loop passes through said proximal and distal elongated slots and under said mid-section of said tissue anchor for coupling said tissue anchor with said suture loop, and wherein said tissue anchor is free to rotate into different orientations relative to said closed end of said suture loop.

6. The system as claimed in claim 1, wherein said pledget comprises:
    a first end having an angled face and a second end having a recess;
    an elongated slot that extends from said angled face of said pledget toward said second end of said pledget;
    an elongated conduit that extends from said elongated slot to said recess at said second end of said pledget;
    wherein said second end of said suture passes in series through said elongated slot, said elongated conduit and into said recess, and wherein said second end of said suture comprises said knot disposed in said recess of said pledget, said knot having a larger diameter than the diameter of said elongated conduit of said pledget.

7. The system as claimed in claim 6, wherein after said tensioner is pulled away from said tissue anchor, said elongated slot of said pledget opposes said top side of said tissue anchor and said slip knot is aligned with said elongated slot.

8. The system as claimed in claim 1, wherein said tensioner comprises a proximal end, a distal end, a recess located at said proximal end, and a channel extending from a distal end of said recess to said distal end of said tensioner, wherein said recess of said tensioner has a larger diameter than said channel of said tensioner, and wherein said first end of said suture passes in series through said channel and into said recess of said tensioner, and wherein said first end of said suture comprises a knot disposed in said recess of said tensioner having a larger diameter than the diameter of said channel of said tensioner.

9. The system as claimed in claim 1, wherein said delivery device further comprises:
    a cartridge for said suture implant secured to said distal end of said elongated shaft, said cartridge having a tube shaped body with a proximal end and a distal end;
    a tensioner channel at said proximal end of said tube shaped body adapted to receive said tensioner;
    a proximal suture slot that extends from said proximal end toward said distal end of said tube shaped body;
    a pledget opening located at a distal end of said proximal suture slot for inserting said pledget into said tube shaped body;
    a distal suture slot that extends from said pledget opening to said distal end of said tube shaped body, wherein said pledget opening is wider than the width of said proximal and distal suture slots.

10. The system as claimed in claim 9, wherein said cartridge comprises a distal end cap secured to said distal end of said tube shaped body having a larger outer diameter than an outer diameter of said tube shaped body to define a stop at a proximal end of said distal end cap.

11. The system as claimed in claim 10, wherein said cartridge comprises a pair of pins projecting away from one another on opposite sides of said tube shaped body, and wherein said distal end of said elongated shaft comprises a pair of slots adapted to receive said pins for securing said cartridge to said distal end of said elongated shaft.

12. The system as claimed in claim 11, wherein said cartridge further comprises:
    an upper channel that extends along the length of said tube shaped body to said distal end of said distal end cap;
    a lower channel that extends along the length of said tube shaped body to said distal end of said distal end cap, wherein said pledget is disposed in said upper channel, said tissue anchor is disposed in said lower channel, said suture loop extends between said pledget and said tissue anchor, and said tensioner is disposed in said tensioner channel.

13. The system as claimed in claim 12, wherein said slip knot is disposed within said upper channel and is located between said pledget and said tissue anchor, wherein said tensioner channel is in axial alignment with said upper channel, and wherein said first end of said suture material extends in said tensioner channel between said pledget and said tensioner.

14. The system as claimed in claim 13, wherein said cartridge comprises a hard stop disposed between a distal end of said tensioner channel and a proximal end of said upper channel, wherein said tensioner is proximal to said hard stop and said pledget is distal to said hard stop.

15. The system as claimed in claim 12, wherein said delivery device further comprises:
a tissue anchor driver disposed within said lower channel of said cartridge;
an actuator for advancing said tissue anchor driver toward said distal end of said elongated shaft for dispensing said tissue anchor from said lower channel of said cartridge.

16. The system as claimed in claim 1, further comprising:
said tensioner including a recess disposed inside said tensioner that is located at a proximal end of said tensioner, wherein said first end of said suture comprises a knot disposed in said recess of said tensioner.

17. A system for deploying a suture implant into tissue comprising:
a delivery device having a handle, an elongated shaft extending from said handle, a driver disposed within said elongated shaft, and an actuator coupled with said driver for advancing said driver toward said distal end of said elongated shaft;
a suture implant disposed at said distal end of said elongated shaft, said suture implant including
a suture having a first end, a second end, and a slip knot located between said first and second ends to define a suture loop having a length, wherein said slip knot defines a dynamic end of said suture loop that is opposite a closed end of said suture loop,
a tissue anchor having first and second openings that are spaced from one another, wherein said closed end of said suture loop passes through said first and second spaced openings for securing said tissue anchor to said suture loop,
a tensioner secured to said first end of said suture,
a pledget secured to said second end of said suture and being located between said tensioner and said tissue anchor, said pledget including a recess disposed inside said pledget that is located at a proximal end of said pledget, wherein said second end of said suture comprises a knot disposed in said recess of said pledget, and
said slip knot being located between said tensioner and said tissue anchor, wherein said tensioner is configured to be pulled away from said tissue anchor for sliding said pledget and said slip knot toward said tissue anchor for shortening the length of said suture loop and reducing the distance between said pledget and said tissue anchor.

18. The system as claimed in claim 17, wherein a distal end of said driver is aligned with said tissue anchor, and wherein said actuator is engageable for dispensing said tissue anchor from said distal end of said elongated shaft.

19. The system as claimed in claim 18, further comprising a cartridge for said suture implant secured to said distal end of said elongated shaft, said cartridge comprising:
a tube shaped body having a proximal end, a distal end, and a length that extends between said proximal and distal ends thereof;
a tensioner channel at said proximal end of said tube shaped body;
a proximal suture slot that extends from said proximal end of said tube shaped body toward said distal end of said tube shaped body;
a pledget opening located at a distal end of said proximal suture slot for inserting said pledget into said tube shaped body;
a distal suture slot that extends from said pledget opening to said distal end of said tube shaped body, wherein said pledget opening is wider than the width of said proximal and distal suture slots.

20. The system as claimed in claim 19, wherein said tube shaped body further comprises:
an upper channel that extends along the length of said tube shaped body to said distal end of said tube shaped body, wherein said upper channel is in axial alignment with said tensioner channel;
a hard stop disposed between a distal end of said tensioner channel and a proximal end of said upper channel;
a lower channel that extends along the length of said tube shaped body to said distal end of said tube shaped body;
said pledget being disposed in said upper channel;
said tensioner being disposed in said tensioner channel, wherein said tensioner is proximal to said hard stop and said pledget is distal to said hard stop;
said tissue anchor being disposed in said lower channel;
said suture loop extending between said tissue anchor in said lower channel and said pledget in said upper channel;
said slip knot being disposed within said upper channel; and
said first end of said suture material extending in said tensioner channel between said pledget and said tensioner.

21. The system as claimed in claim 17, further comprising:
said tensioner including a recess disposed inside said tensioner that is located at a proximal end of said tensioner, wherein said first end of said suture comprises a knot disposed in said recess of said tensioner.

22. A system for deploying a suture implant into tissue comprising:
a delivery device having an elongated shaft, a driver disposed within said elongated shaft, and an actuator for advancing said driver toward said distal end of said elongated shaft;
a suture implant cartridge secured to said distal end of said elongated shaft;
a suture implant loaded into said suture implant cartridge, said suture implant including
a suture having a first end, a second end, and a slip knot located between said first and second ends to define a suture loop having a length, wherein said slip knot defines a dynamic end of said suture loop that is opposite a closed end of said suture loop,
a tissue anchor having first and second openings that are spaced from one another, wherein said closed end of said suture loop passes through said first and second spaced openings for securing said tissue anchor to said suture loop, a tensioner secured to said first end of said suture, a pledget secured to said second end of said suture and being located between said tensioner and said tissue anchor, said pledget including a recess disposed inside said pledget that is located at a proximal end of said pledget, wherein said second end of said suture comprises a knot disposed in said recess of said pledget, and said slip knot being located between said tensioner and said tissue anchor, wherein said delivery device has a first dispensing stage during which said driver moves distally for dispensing said tissue anchor from said cartridge, and a second dispensing stage during which said tensioner is pulled away from said tissue anchor for sliding said pledget and said slip knot toward said tissue anchor to shorten the length of said suture loop and reduce the distance between said pledget and said tissue anchor.

23. The system as claimed in claim 22, further comprising:

said tensioner including a recess disposed inside said tensioner that is located at a proximal end of said tensioner, wherein said first end of said suture comprises a knot disposed in said recess of said tensioner.

\* \* \* \* \*